United States Patent
Niesman et al.

(10) Patent No.: US 11,154,555 B2
(45) Date of Patent: Oct. 26, 2021

(54) TREATMENT OF CANCER

(71) Applicant: MingSight Pharmaceuticals, Inc., San Diego, CA (US)

(72) Inventors: Michael Niesman, San Diego, CA (US); Kai Zhang, San Diego, CA (US)

(73) Assignee: MINGSIGHT PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 16/317,520

(22) PCT Filed: Jul. 13, 2017

(86) PCT No.: PCT/US2017/042011
§ 371 (c)(1),
(2) Date: Jan. 11, 2019

(87) PCT Pub. No.: WO2018/013862
PCT Pub. Date: Jan. 18, 2018

(65) Prior Publication Data
US 2019/0216809 A1    Jul. 18, 2019

Related U.S. Application Data

(60) Provisional application No. 62/362,369, filed on Jul. 14, 2016.

(51) Int. Cl.
| | | |
|---|---|---|
| *A61K 31/506* | (2006.01) | |
| *A61K 31/519* | (2006.01) | |
| *A61K 45/06* | (2006.01) | |
| *A61P 35/02* | (2006.01) | |
| *A61P 35/00* | (2006.01) | |

(52) U.S. Cl.
CPC .......... *A61K 31/506* (2013.01); *A61K 31/519* (2013.01); *A61K 45/06* (2013.01); *A61P 35/00* (2018.01); *A61P 35/02* (2018.01)

(58) Field of Classification Search
CPC .............. A61K 2300/00; A61K 31/506; A61K 31/519; A61K 45/06; A61P 35/00; A61P 35/02
See application file for complete search history.

(56) References Cited

U.S. PATENT DOCUMENTS

| | | |
|---|---|---|
| 8,114,871 B2 | 2/2012 | Botrous et al. |
| 8,183,255 B2 | 5/2012 | Li et al. |
| 8,877,761 B2 | 11/2014 | Li et al. |
| 8,999,981 B2 | 4/2015 | Botrous et al. |
| 9,518,060 B2 | 12/2016 | Li et al. |
| 2007/0276088 A1 | 11/2007 | Maynard et al. |
| 2015/0260723 A1 | 9/2015 | Chang et al. |
| 2017/0335281 A1 | 11/2017 | Loew et al. |
| 2017/0340733 A1 | 11/2017 | Cao |
| 2021/0069194 A1 | 3/2021 | Niesman et al. |

FOREIGN PATENT DOCUMENTS

| | | | |
|---|---|---|---|
| CN | 101646673 A | 2/2010 | |
| WO | WO-2008096260 A1 * | 8/2008 | ........... C07D 487/04 |
| WO | WO-2008125945 A2 | 10/2008 | |
| WO | WO-2011120911 A1 | 10/2011 | |
| WO | WO-2014168975 A1 | 10/2014 | |
| WO | WO-2015110923 A2 | 7/2015 | |
| WO | WO-2015146159 A1 | 10/2015 | |
| WO | WO-2015179847 A1 | 11/2015 | |
| WO | WO-2016020864 A1 | 2/2016 | |
| WO | WO-2018013862 A1 | 1/2018 | |
| WO | WO-2019143818 A1 | 7/2019 | |

OTHER PUBLICATIONS

El-Gamal et al., BLOOD, Aug. 28, 2014, vol. 124, No. 9. (Year: 2014).*
Abdul-Aziz et al. MIF-Induced Stromal PKCβ/IL8 Is Essential in Human Acute Myeloid Leukemia. Cancer Res 77(2):303-311 (2017).
Chou. Drug Combination Studies and Their Synergy Quantification Using the Chou-Talalay Method. Cancer Res 70(2):440-446 (2010).
Chou. Theoretical Basis, Experimental Design, and Computerized Simulation of Synergism and Antagonism in Drug Combination Studies, Pharmacol Rev 58:621-681 (2006).
Das Evcimen et al. The role of protein kinase C activation and the vascular complications of diabetes. Pharmacol Res 55(6):498-510 (2007).
Dufies et al. Mechanisms of AXL overexpression and function in Imatinib-resistant chronic myeloid leukemia cells. Oncotarget 2:874-885 (2011).
Gruber et al. PKCθ cooperates with PKCα in alloimmune responses of T cells in vivo. Mol Immunol 46:2071-2079 (2009).
Leitges et al. Immunodeficiency in protein kinase Cβ-deficient mice. Science 273:788-791 (1996).
Li et al. A novel bisindolymaleimide derivative (WK234) inhibits proliferation and induces apoptosis through the protein kinase Cβ pathway, in chronic myelogenous leukemia K562 cells Leuk Lymphoma 52(7):1312-1320 (2011).
Marsland et al. T-cell fate and function: PKC-θ and beyond. Trends Immunol 29(4):179-185 (2008).
Mecklenbrauker et al. Protein kinase Cδ controls self-antigen-induced B-cell tolerance. Nature 416:860-865 (2002).
Miyamoto et al. Increased proliferation of B cells and auto-immunity in mice lacking protein kinase Cdelta. Nature 416, 865-869.
Newton. Protein kinase C: structural and spatial regulation by phosphorylation, cofactors, and macromolecular interactions. Chem Rev 101:2353-2364 (2001).

(Continued)

*Primary Examiner* — Jean P Cornet
(74) *Attorney, Agent, or Firm* — Wilson Sonsini Goodrich & Rosati

(57) ABSTRACT

Provided herein are compositions and methods for the treatment of a hematological malignancy. Also disclosed herein are compositions and methods for the treatment of Ewings Sarcoma. Said compositions comprise isoform selective pyrrolo-pyrazole PKC inhibitors.

7 Claims, 7 Drawing Sheets

(56) References Cited

OTHER PUBLICATIONS

Patani et al. Bioisosterism: A Rational Approach in Drug Design. Chemical Reviews 96:3147-3176 (1996).
PCT/US2017/042011 International Search Report and Written Opinion dated Dec. 4, 2017.
PCT/US2017/042011 Invitation to Pay Additional Fees dated Oct. 4, 2017.
Pfeifhofer et al. Defective IgG2a/2b class switching in PKC alpha-/- mice. J Immunol 176:6004-6011 (2006).
Saba et al. Apoptotic induction in B-cell acute lymphoblastic leukemia cell lines treated with a protein kinase Cβ inhibitor. Leuk Lymphoma 52(5):877-886 (2011).
Saijo et al. Protein kinase C β controls nuclear factor κB activation in B cells through selective regulation of the IκB kinase α. J Exp Med 195:1647-1652 (2002).
Su et al. PKC-β controls IκB kinase lipid raft recruitment and activation in response to BCR signaling. Nat Immunol 3:780-786 (2002).
Sun. Intervention of PKC-θ as an immunosuppressive regimen. Front Immunol 3:225 (2012).
Von Essen et al. Protein kinase C (PKC)α and PKCθ are the major PKC isotypes involved in TCR down-regulation. J Immunol 176:7502-7510 (2006).
Wahren-Herlenius et al. Immunopathogenic mechanisms of systemic autoimmune disease. Lancet 382:819-831 (2013).
D'Cruz et al. Protein kinase inhibitors against malignant lymphoma. Expert Opinion on Pharmacotherapy 14(6):707-721 (2013).
Evenou et al. The Potent Protein Kinase C-selective Inhibitor AEB071 (Sotrastaurin) Represents a New Class of Immunosuppressive Agents Affecting Early T-cell Activation. J Pharmacol Exp Ther 330(3):792-801 (2009).
Skvara et al. The PKC inhibitor AEB071 may be a therapeutic option for psoriasis. J Clin Invest 118(9):3151-3159 (2008).
Antal et al. Cancer-Associated Protein Kinase C Mutations Reveal Kinase's Role as Tumor Suppressor. Cell 160(3):489-502 (2015).
Bourhill et al. Enzastaurin: A lesson in drug development. Crit Rev Oncol Hematol 112:72-79 (2017).
Carducci et al. Phase I Dose Escalation and Pharmacokinetic Study of Enzastaurin, an Oral Protein Kinase C Beta Inhibitor, in Patients With Advanced Cancer. J Clin Oncol 24(25):4092-9 (2006).
Fraietta et al. Ibrutinib enhances chimeric antigen receptor T-cell engraftment and efficacy in leukemia. Blood 127(9):1117-1127 (2016).
Friman et al. Sotrastaurin, a novel small molecule inhibiting protein-kinase C: randomized phase II study in renal transplant recipients. Am J Transplant 11(7):1444-55 (2011).
Gill et al. Reply to M. Uccello et al. J Clin Oncol 35:1371 (2017).
Herman et al., Ibrutinib-induced lymphocytosis in patients with chronic lymphocytic leukemia: correlative analyses from a phase II study. Leukemia, 28:2188-2196 (2014).
Hing et al. Selinexor is effective in acquired resistance to ibrutinib and synergizes with ibrutinib in chronic lymphocytic leukemia. Blood 125:3128-3132 (2015).
Lapalombella et al. Selective inhibitors of nuclear export show that CRM1/XPO1 is a target in chronic lymphocytic leukemia. Blood 120:4621-34 (2012).
Morschhauser et al. A phase II study of enzastaurin, a protein kinase C beta inhibitor, in patients with relapsed or refractory mantle cell lymphoma. Ann Oncol 19(2):247-53 (2008).
Naylor et al. Protein kinase C inhibitor sotrastaurin selectively inhibits the growth of CD79 mutant diffuse large B-cell lymphomas. Cancer Res 71:2643-2653 (2011).
PCT/US2019/014015 International Search Report and Written Opinion dated Apr. 12, 2019.
Ruella et al. Kinase inhibitor ibrutinib to prevent cytokine-release syndrome after anti-CD19 chimeric antigen receptor T cells for B-cell neoplasms. Leukemia 31:246-248 (2017).
Ruella et al. The Addition of the BTK Inhibitor Ibrutinib to Anti-CD19 Chimeric Antigen Receptor T Cells (CART19) Improves Responses against Mantle Cell Lymphoma. Clin Cancer Res 22:2684-2696 (2016).
Welch et al. Safety, tolerability, QTc evaluation, and pharmacokinetics of single and multiple doses of enzastaurin HCl (LY317615), a protein kinase C-beta inhibitor, in healthy subjects. J Clin Pharmcol 47(9):1138-51 (2007).
Woyach et al. Bruton's tyrosine kinase (BTK) function is important to the development and expansion of chronic lymphocytic leukemia (CLL). Blood 123:1207-13 (2014).
Woyach et al. Prolonged lymphocytosis during ibrutinib therapy is associated with distinct molecular characteristics and does not indicate a suboptimal response to therapy. Blood 123(12):1810-7 (2014).
Furman et al. CAL-101, An Isoform-Selective Inhibitor of Phosphatidylinositol 3-Kinase P110δ, Demonstrates Clinical Activity and Pharmacodynamic Effects In Patients with Relapsed or Refractory Chronic Lymphocytic Leukemia. Blood 116(21):55 (2010) (Abstract).
Kim et al. Protein kinase C-associated kinase is required for NF-kappaB signaling and survival in diffuse large B-cell lymphoma cells. Blood 111(3): 1644-53 (2008).
Muhowski et al. The Protein Kinase C Inhibitor MS-553 for the Treatment of Chronic Lymphocytic Leukemia. Blood 134(Supplement_1):2077 (2019).
Zhang et al. Mechanisms of ibrutinib resistance in chronic lymphocytic leukaemia and non-Hodgkin lymphoma. Br J Haematol 170(4):445-56 (2015).
Li et al., Retrospective analysis of protein kinase C-beta (PKC-beta) expression in lymphoid malignancies and its association with survival in diffuse large B-cell lymphomas. Biol Direct 2:8 (2007).

\* cited by examiner

TREATMENT OF CANCER

CROSS-REFERENCE

This application is a U.S. National Stage of PCT/US2017/042011, filed Jul. 13, 2017, which claims the benefit of U.S. Provisional Application No. 62/362,369, filed Jul. 14, 2016, all of which are incorporated herein by reference in their entirety.

BRIEF SUMMARY OF THE INVENTION

Provided herein are compositions and methods for the treatment of cancer. The types of cancer suitable for the methods disclosed herein include, but are not limited to, hematological malignancy and Ewing's Sarcoma. The compositions useful for the methods of treating cancer disclosed herein comprise pyrrolo-pyrazole PKC inhibitors.

One embodiment provides a method of treating a hematological malignancy in a subject in need thereof comprising administering to the subject a composition comprising a compound having the formula 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and a pharmaceutically acceptable excipient.

INCORPORATION BY REFERENCE

Figure 1A:
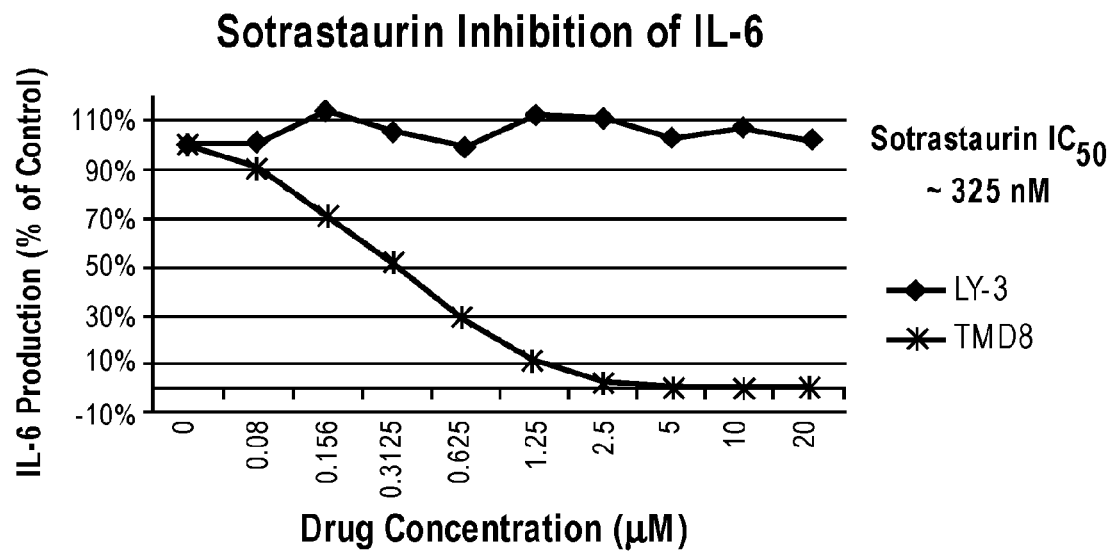
FIGS. 1A-B shows the dose dependent inhibition of IL-6 production in TMD8 and OCI-Ly3 cells exposed to Compound A (FIG. 1B) or sotrastaurin (FIG. 1A).

All publications, patents, and patent applications mentioned in this specification are herein incorporated by reference for the specific purposes identified herein.

DETAILED DESCRIPTION OF THE INVENTION

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 μg" means "about 5 μg" and also "5 μg." Generally, the term "about" includes an amount that would be expected to be within experimental error.

As used herein, the terms "comprising" and "including" are used in their open, non-limiting sense. As used herein, the terms "$C_1$-$C_8$" or "$C_2$-$C_8$" and so forth, refer to moieties having 1 to 8 or 2 to 8 carbon atoms, respectively.

The term "alkyl", as used herein, unless otherwise indicated, includes saturated monovalent hydrocarbon radicals having straight or branched moieties. Exemplary alkyl moieties have carbon atoms in the range of 1 to 8 carbon atoms, 1 to 6 carbon atoms or 1 to 4 carbon atoms.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxyl", as used herein, unless otherwise indicated, includes O-alkyl groups wherein alkyl is as defined above.

The term "hydroxyl", as used herein, unless otherwise indicated, includes —OH.

The term "amino", as used herein, unless otherwise indicated, is intended to include the —$NH_2$ radical, and any substitutions of the N atom.

The terms "halogen" and "halo", as used herein, unless otherwise indicated, represent chlorine, fluorine, bromine or iodine.

The term "trifluoromethyl", as used herein, unless otherwise indicated, is meant to represent a —$CF_3$ group.

The term "perfluoroalkyl", as used herein, is meant to represent an alkyl group in which all hydrogens attached to the carbons have been replaced by fluorine, such as $CF_3$, $CF_2$—$CF_3$, $C(CF_2)(CF_2)$ and so on.

The term "trifluoromethoxy", as used herein, unless otherwise indicated, is meant to represent a —$OCF_3$ group.

The term "cyano", as used herein, unless otherwise indicated, is meant to represent a—CN group.

The term "$CH_2Cl_2$", as used herein, unless otherwise indicated, is meant to represent dichloromethane.

The term "$C_3$-$C_{12}$ cycloalkyl" or "$C_5$-$C_8$ cycloalkyl", as used herein, unless otherwise indicated, refers to a non-aromatic, saturated or partially saturated, monocyclic or fused, spiro or unfused bicyclic or tricyclic hydrocarbon referred to herein containing a total of from 3 to 12 carbon atoms, or 5-8 ring carbon atoms, respectively. Exemplary cycloalkyls include rings having from 3-10 carbon atoms, such as cyclopropyl, cyclobutyl, cyclopentyl, cyclohexyl, cycloheptyl, and adamantyl. Illustrative examples of cycloalkyl are derived from, but not limited to, the following:

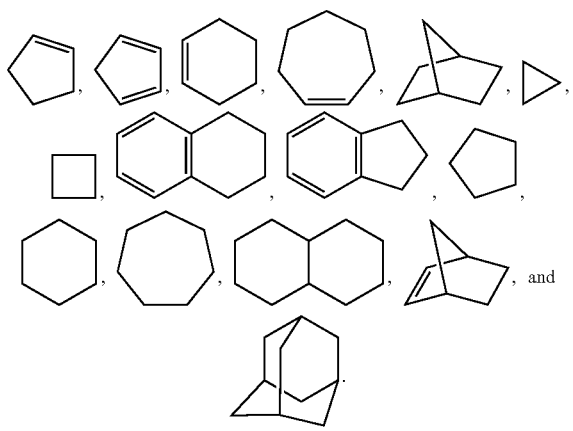

The term "aryl", as used herein, unless otherwise indicated, includes an organic radical derived from an aromatic hydrocarbon by removal of one hydrogen, such as phenyl or naphthyl.

The term "(3-15)-membered heterocycyl", "(3-7)-membered heterocyclyl", "(6-10)-membered heterocyclyl", or "(4 to 10)-membered heterocyclyl", as used herein, unless otherwise indicated, includes aromatic and non-aromatic heterocyclic groups containing one to four heteroatoms each selected from O, S and N, wherein each heterocyclic group has from 3-15, 3-7, 6-10, or 4 to 10 atoms, respectively, in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3 membered heterocyclic group is aziridine, an example of a 4 membered heterocyclic group is azetidinyl (derived from azetidine). An example of a 5 membered heterocyclic group is thiazolyl, an example of a 7 membered ring is azepinyl, and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Heterocycles include monocyclic and polycyclic aromatic ring structures, with "(5-12)-membered heteroaryls" referring to those that are heterocycles having 5 to 12 atoms in their ring system(s). Examples of "(5-12)-membered heteroaryls" are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The above-mentioned heterocyclic groups may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other illustrative examples of 4 to 10 membered heterocyclic are derived from, but not limited to, the following:

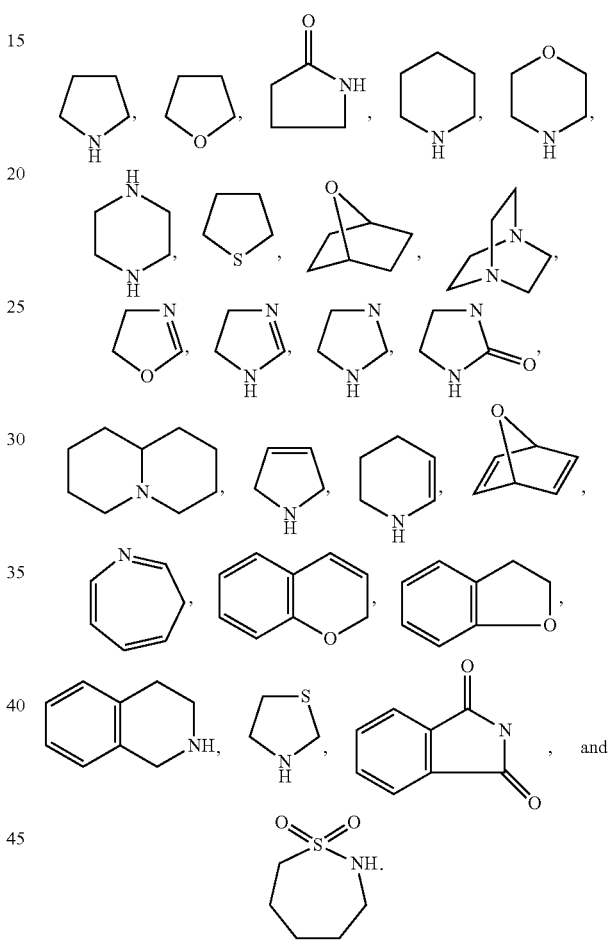

The term "(12-15)-membered heterocyclyl", as used herein, unless otherwise indicated, includes aromatic and non-aromatic heterocyclic groups that are in a partially fused or spirocyclic configuration and which contain at least one N and optionally additional 1 to 5 heteroatoms each selected from O, S and N, wherein the heterocyclic group has from 12 to 15 atoms, respectively, in its system, and with the proviso that any ring of said group does not contain two adjacent O or S atoms. The heterocyclic groups include tricyclic fused ring and spirocyclic systems. An example of a 13-membered tricyclic heterocyclic group is 3,4-dihydropyrazino[1,2-a]benzimidazole and an example of a 15-membered spirocyclic heterocyclic group is 3,4-dihydro-1'H-spirochromene.

Unless otherwise indicated, the term "oxo" refers to =O.

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO (dimethylsulfoxide), ethyl acetate, acetic acid, or ethanolamine.

The phrase "pharmaceutically acceptable salt(s)", as used herein, unless otherwise indicated, includes salts of acidic or basic groups which may be present in the compounds of formula (I), formula (A) or formula (B). The compounds of formula (I), formula (A) or formula (B) that are basic in nature are capable of forming a wide variety of salts with various inorganic and organic acids. The acids that may be used to prepare pharmaceutically acceptable acid addition salts of such basic compounds of formula (I), formula (A) or formula (B) are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

The term "treating", as used herein, unless otherwise indicated, means reversing, alleviating, inhibiting the progress of, or preventing the disorder or condition to which such term applies, or one or more symptoms of such disorder or condition. In some embodiments, the term "treating" includes slowing or delaying the progression of the disease or disorder to which the term is applied. Additionally, in some embodiments, the term "treating" is applied to one or more of the complications resulting from the disease or disorder to which the term is applied. The term "treatment", as used herein, unless otherwise indicated, refers to the act of treating as "treating" is defined immediately above.

The phrase "therapeutically effective amount", as used herein, refers to that amount of drug or pharmaceutical agent that will elicit the biological or medical response of a tissue, system, animal, or human that is being sought by a researcher, veterinarian, medical doctor or other.

The term "substituted" means that the specified group or moiety bears one or more substituents. The term "unsubstituted" means that the specified group bears no substituents. The term "optionally substituted" means that the specified group is unsubstituted or substituted by one or more substituents.

In accordance with convention, in some structural formula herein, the carbon atoms and their bound hydrogen atoms are not explicitly depicted e.g.,

represents a methyl group, represents an ethyl group,

represents a cyclopentyl group, etc. Moreover, the depiction of any cyclic group (aryl, heterocyclic or cycloalkyl) with a bond that is not directly attached to a ring atom, e.g.,

indicates that the point of attachment may be on any available ring atom of the cyclic group.

Certain compounds utilized in the methods disclosed herein may have asymmetric centers and therefore exist in different enantiomeric forms. All optical isomers and stereoisomers of the compounds utilized in the methods disclosed herein, and mixtures thereof, are considered to be within the scope of the invention. With respect to the compounds utilized in the methods disclosed herein, the invention includes the use of a racemate, one or more enantiomeric forms, one or more diastereomeric forms, or mixtures thereof. The compounds utilized in the methods disclosed herein may also exist as tautomers. This invention relates to the use of all such tautomers and mixtures thereof.

Certain functional groups contained within the compounds of the present invention can be substituted for bioisosteric groups, that is, groups which have similar spatial or electronic requirements to the parent group, but exhibit differing or improved physicochemical or other properties. Suitable examples are well known to those of skill in the art, and include, but are not limited to moieties described in Patini et al., Chem. Rev, 1996, 96, 3147-3176 and references cited therein.

The subject invention also includes isotopically-labelled compounds, which are identical to the compounds utilized in the methods disclosed herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention and pharmaceutically acceptable salts or solvates of said compounds which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds utilized in the methods disclosed herein can generally be prepared by carrying out the procedures disclosed in the Schemes and/or in the Examples below, by substituting a readily available isotopically labeled reagent for a non-isotopically labeled reagent.

The term "mmol", as used herein, unless otherwise indicated, is intended to mean millimole. The term "equiv", as used herein, unless otherwise indicated, is intended to mean equivalent. The term "mL", as used herein, unless otherwise indicated, is intended to mean milliliter. The term "U", as used herein, unless otherwise indicated, is intended to mean units. The term "mm" as used herein, unless otherwise indicated, is intended to mean millimeter. The term "g", as used herein, unless otherwise indicated, is intended to mean gram. The term "kg", as used herein, unless otherwise indicated, is intended to mean kilogram. The term "h", as used herein, unless otherwise indicated, is intended to mean hour. The term "min", as used herein, unless otherwise indicated, is intended to mean minute. The term "μL", as used herein, unless otherwise indicated, is intended to mean microliter. The term "μM", as used herein, unless otherwise indicated, is intended to mean micromolar. The term "μm", as used herein, unless otherwise indicated, is intended to mean micrometer. The term "M", as used herein, unless otherwise indicated, is intended to mean molar. The term "N", as used herein, unless otherwise indicated, is intended to mean normal. The term "nm", as used herein, unless otherwise indicated, is intended to mean nanometer. The term "nM", as used herein, unless otherwise indicated, is intended to mean nanoMolar. The term "amu", as used herein, unless otherwise indicated, is intended to mean atomic mass unit. The term "° C.", as used herein, unless otherwise indicated, is intended to mean Celsius. The term "m/z", as used herein, unless otherwise indicated, is intended to mean, mass/charge ratio. The term "wt/wt", as used herein, unless otherwise indicated, is intended to mean weight/weight. The term "v/v", as used herein, unless otherwise indicated, is intended to mean volume/volume. The term "mL/min", as used herein, unless otherwise indicated, is intended to mean milliliter/minute. The term "UV", as used herein, unless otherwise indicated, is intended to mean ultraviolet. The term "APCI-MS", as used herein, unless otherwise indicated, is intended to mean atmospheric pressure chemical ionization mass spectroscopy. The term "HPLC", as used herein, unless otherwise indicated, is intended to mean high performance liquid chromatograph. The chromatography was performed at a temperature of about 20° C., unless otherwise indicated. The term "LC", as used herein, unless otherwise indicated, is intended to mean liquid chromatograph. The term "LCMS", as used herein, unless otherwise indicated, is intended to mean liquid chromatography mass spectroscopy. The term "TLC", as used herein, unless otherwise indicated, is intended to mean thin layer chromatography. The term "SFC", as used herein, unless otherwise indicated, is intended to mean supercritical fluid chromatography. The term "sat" as used herein, unless otherwise indicated, is intended to mean saturated. The term "aq" as used herein, is intended to mean aqueous. The term "ELSD" as used herein, unless otherwise indicated, is intended to mean evaporative light scattering detection. The term "MS", as used herein, unless otherwise indicated, is intended to mean mass spectroscopy. The term "HRMS (ESI)", as used herein, unless otherwise indicated, is intended to mean high-resolution mass spectrometry (electrospray ionization). The term "Anal.", as used herein, unless otherwise indicated, is intended to mean analytical. The term "Calcd", as used herein, unless otherwise indicated, is intended to mean calculated. The term "N/A", as used herein, unless otherwise indicated, is intended to mean not tested. The term "RT", as used herein, unless otherwise indicated, is intended to mean room temperature. The term "Mth.", as used herein, unless otherwise indicated, is intended to mean Method. The term "Celite", as used herein, unless otherwise indicated, is intended to mean a white solid diatomite filter agent commercially available from World Minerals located in Los Angeles, Calif. USA. The term "Eg.", as used herein, unless otherwise indicated, is intended to mean example.

Terms such as $-(CR^3R^4)_t$ or $-(CR^{10}R^{11})_v$, for example, are used, $R^3$, $R^4$, $R^{10}$ and $R^{11}$ may vary with each iteration of t or v above 1. For instance, where t or v is 2 the terms $-(CR^3R^4)_v$ or $-(CR^{10}R^{11})_t$ may equal $-CH_2CH_2-$, or $-CH(CH_3)C(CH_2CH_3)(CH_2CH_2CH_3)-$, or any number of similar moieties falling within the scope of the definitions of $R^3$, $R^4$, $R^{10}$ and $R^{11}$.

The term "$K_i$", as used herein, unless otherwise indicated, is intended to mean values of enzyme inhibition constant. The term "$K_i$ app", as used herein, unless otherwise indicated, is intended to mean $K_i$ apparent. The term "$IC_{50}$", as used herein, unless otherwise indicated, is intended to mean concentrations required for at least 50% enzyme inhibition.

Other aspects, advantages, and features of the invention will become apparent from the detailed description below.

Protein Kinase C

The superfamily of kinases known as protein kinase C (PKC) are important kinases that are active in and that act as regulators in many cell signaling pathways. (Newton, 2001, Chem. Rev. 101, 2353-2364). Specific isoforms of PKC have been implicated in the response to hyperglycemia (e.g., PKCβ (beta) Das Evcimen and King, 2007, Pharmacol Res,. 55(6): p. 498-510) and in T and B cell survival and function (e.g., PKCθ (theta): Sun, Z. 2012, Front Immunol 3, 225; PKCβ: Leitges, M. et al., 1996, Science 273, 788-791; PKCα (alpha): Gruber, T. et al., 2009, Mol Immunol 46, 2071-2079).

Both T lymphocytes and B lymphocytes (T cells and B cells) have been shown to contribute to autoimmune disease, often simultaneously (Wahren-Herlenius and Dörner T. 2013, Lancet. 382:819-31). Recent scientific reports have revealed that specific isoforms of PKC are crucial to the normal function of T and B cells and in their contribution to autoimmune disease.

Three isoforms, PKCθ, PKCα and PKCβ, appear to be most important for lymphocyte function. PKCθ is critical to T-cell function (Sun, 2012, Front Immunol 3, 225). Specifically, PKCθ is downstream of the T cell receptor complex and plays a critical role in T cell survival, function and autoimmune stimulation. Mouse models of autoimmune diseases have been used to illustrate PKCθ function in T cell-dependent autoimmunity (Marsland, B. J. and Kopf, M., 2008, Trends Immunol, 29(4) 179-85). PKCα plays a non-redundant role in T cell activation (Gruber, T., et al, 2009, Mol Immunol 46, 2071-2079; Pfeifhofer, C., et al, 2006, J Immunol 176, 6004-6011; von Essen, M., et al, 2006, J Immunol 176, 7502-75). And PKCβ plays a key role in B cell survival, function, and the dysfunction seen in autoimmunity (Leitges, M., et al, 1996, Science 273, 788-791; Saijo, K., et al, 2002, J Exp Med 195, 1647-1652; Su, T. T., et al., 2002, Nat Immunol 3, 780-786). Finally, it has been shown in mice that inhibition of PKCδ (delta) appears to have the potential to induce autoimmune disease in B cells. PKCδ knockout mice (PKCδ ) have increased antibody production including auto-antibodies and actually display autoimmune phenotypes. (Mecklenbrauker, I., et al, 2002, Nature 416, 860-865; Miyamoto, A., et al., 2002, Nature 416, 865-869).

The technical problem to be solved in the use of PKC inhibitors for the treatment of cancer is the inhibition of the correct PKC isoform(s) without inhibiting critical PKC isoforms, such as PKCδ. Provided herein is a solution to this problem in that the pyrrolo-pyrazole PKC inhibitors described herein are isoform selective PKC inhibitors which lack, in the least, PKGδ activity.

Pyrrolo-pyrazole PKC Inhibitors

The pyrrolo-pyrazole PKC inhibitors used herein have been previously described in WO 2008/096260 and WO 2008/125945 and related patents and patent applications, e.g. U.S. Pat. Nos. 8,183,255, 8,877,761, 9,518,060, 8,114,871, and 8,999,981, each of which is incorporated by reference in their entirety. As used herein, the term compound A (or cmpd A) refers to 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, which was disclosed in WO 2008/096260 and has the chemical structure shown below.

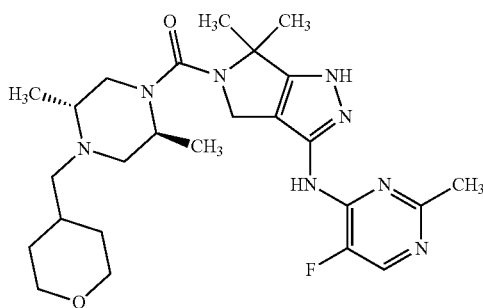 [SMILES: Cc1ncc(F)c(Nc2n[nH]c3c2CN(C(=O)N2C[C@@H](C)N(CC4CCOCC4)C[C@@H]2C)C3(C)C)n1]

Hematological Malignancies

Hematological malignancies are cancers that affect the blood and lymph system. The cancer may begin in blood-forming tissue (e.g., bone marrow), or in the cells of the immune system. In some embodiments, a hematologic malignancy is a leukemia, a non-Hodgkin lymphoma (NHL), a Hodgkin lymphoma, or a multiple myeloma. Hematological malignancies can originate either in the lymphatic tissues (e.g., lymphoma) or in the bone marrow (e.g., leukemia and myeloma), and all involve the uncontrolled growth of lymphocytes or white blood cells.

Malignant lymphomas are neoplastic transformations of cells that reside predominantly within lymphoid tissues. Two groups of malignant lymphomas are Hodgkin's lymphoma and non-Hodgkin's lymphoma (NHL). Both types of lymphomas infiltrate reticuloendothelial tissues. However, they differ in the neoplastic cell of origin, site of disease, presence of systemic symptoms, and response to treatment. Non-Hodgkin lymphomas (NHL) are a diverse group of malignancies that are predominately of B-cell origin. NHL may develop in any organs associated with the lymphatic system such as the spleen, lymph nodes, or tonsils and can occur at any age. NHL is often marked by enlarged lymph nodes, fever, and weight loss. NHL is classified as either B-cell or T-cell NHL. Although chemotherapy can induce remissions in the majority of indolent lymphomas, cures are rare and most patients eventually relapse, requiring further therapy.

A non-limiting list of the B-cell NHL includes Burkitt's lymphoma (e.g., Endemic Burkitt's Lymphoma and Sporadic Burkitt's Lymphoma), Cutaneous B-Cell Lymphoma, Cutaneous Marginal Zone Lymphoma (MZL), Diffuse Large Cell Lymphoma (DLBCL), Diffuse Mixed Small and Large Cell Lympoma, Diffuse Small Cleaved Cell, Diffuse Small Lymphocytic Lymphoma, Extranodal Marginal Zone B-cell lymphoma, follicular lymphoma, Follicular Small Cleaved Cell (Grade 1), Follicular Mixed Small Cleaved and Large Cell (Grade 2), Follicular Large Cell (Grade 3), Intravascular Large B-Cell Lymphoma, Intravascular Lymphomatosis, Large Cell Immunoblastic Lymphoma, Large Cell Lymphoma (LCL), Lymphoblastic Lymphoma, MALT Lymphoma, Mantle Cell Lymphoma (MCL), immunoblastic large cell lymphoma, precursor B-lymphoblastic lymphoma, mantle cell lymphoma, chronic lymphocytic leukemia (CLL)/small lymphocytic lymphoma (SLL), extranodal marginal zone B-cell lymphoma-mucosa-associated lymphoid tissue (MALT) lymphoma, Mediastinal Large B-Cell Lymphoma, nodal marginal zone B-cell lymphoma, splenic marginal zone B-cell lymphoma, primary mediastinal B-cell lymphoma, lymphoplasmocytic lymphoma, hairy cell leukemia, Waldenstrom's Macroglobulinemia, and primary central nervous system (CNS) lymphoma. Additional non-Hodgkin's lymphomas are contemplated within the scope of the present invention and apparent to those of ordinary skill in the art.

Some patients achieve a remission (an absence of signs and symptoms) after initial treatment for a hematological malignancy. However, other patients have residual cancerous cells in that remain even after intensive treatment.

In some embodiments, an individual has a hematological malignancy that has relapsed after therapeutic treatment. In some embodiments, the hematological malignancy is resistant to therapeutic treatment. In some embodiments, the hematological malignancy has primary resistance to therapeutic treatment. In some embodiments, the hematological malignancy has secondary or acquired resistance to therapeutic treatment. In some embodiments, the hematological malignancy has primary resistance to treatment with a BTK inhibitor. In some embodiments, the hematological malignancy has primary resistance to treatment with irbutinib. In some embodiments, the hematological malignancy has acquired resistance to treatment with a BTK inhibitor. In some embodiments, the hematological malignancy has acquired resistance to treatment with irbutinib. In some embodiments, treatment of a hematological malignancy with a BTK inhibitor is unsuitable or otherwise contraindicated. In some embodiments, treatment of a hematological malignancy with ibritinub is unsuitable or otherwise contraindicated.

Disclosed herein, in some embodiments, are methods of treating a hematological malignancy in an individual in need thereof, comprising administering to the individual a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof.

Disclosed herein, in some embodiments, are methods of treating a hematological malignancy in an individual in need thereof, comprising administering to the individual: (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; and (b) a BTK inhibitor.

Disclosed herein, in some embodiments, are methods of treating a hematological malignancy in an individual in need thereof, comprising administering to the individual: (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; and (b) irbutinib.

DLBCL

Diffuse large B-cell lymphoma (DLBCL) is the most common aggressive lymphoma subtype in western countries, accounting for approximately 30% of new cases of non-Hodgkin's lymphoma (NHL). Genetic tests have shown that there are different subtypes of DLBCL. These subtypes seem to have different outlooks (prognoses) and responses to treatment. At least 3 molecular subtypes of DLBCL can be distinguished: germinal center B-celllike (GCB) DLBCL, activated B-celllike (ABC) DLBCL, and primary mediastinal B-cell lymphoma (PMBL). DLBCL can affect any age group, but occurs mostly in older people (the average age is mid-60s).

The ABC subtype of DLBCL (ABC-DLBCL) accounts for approximately 30% total DLBCL diagnoses. It is considered the least curable of the DLBCL molecular subtypes and, as such, patients diagnosed with the ABC-DLBCL typically display significantly reduced survival rates compared with individuals with other types of DLCBL. ABC-DLBCL is most commonly associated with chromosomal translocations deregulating the germinal center master regulator BCL6 and with mutations inactivating the PRDM1 gene, which encodes a transcriptional repressor required for plasma cell differentiation.

A particularly relevant signaling pathway in the pathogenesis of ABC-DLBCL is the one mediated by the nuclear factor (NF)-κB transcription complex. The NF-κB family comprises 5 members (p50, p52, p65, c-rel and RelB) that form homo- and heterodimers and function as transcriptional factors to mediate a variety of proliferation, apoptosis, inflammatory and immune responses and are critical for normal B-cell development and survival. NF-κB is widely used by eukaryotic cells as a regulator of genes that control cell proliferation and cell survival. As such, many different types of human tumors have misregulated NF-κB: that is, NF-κB is constitutively active. Active NF-κB turns on the expression of genes that keep the cell proliferating and protect the cell from conditions that would otherwise cause it to die via apoptosis.

The dependence of ABC DLBCLs on NF-κB depends on a signaling pathway upstream of IkB kinase comprised of CARD11, BCL10 and MALT1 (the CBM complex). Interference with the CBM pathway extinguishes NF-kB signaling in ABC DLBCL cells and induces apoptosis. The molecular basis for constitutive activity of the NF-kB pathway is a subject of current investigation but some somatic alterations to the genome of ABC DLBCLs clearly invoke this pathway. For example, somatic mutations of the coiled-coil domain of CARD11 in DLBCL render this signaling scaffold protein able to spontaneously nucleate protein-protein interaction with MALT1 and BCL10, causing IKK activity and NF-kB activation. Constitutive activity of the B cell receptor signaling pathway has been implicated in the activation of NF-kB in ABC DLBCLs with wild type CARD11, and this is associated with mutations within the cytoplasmic tails of the B cell receptor subunits CD79A and CD79B. Oncogenic activating mutations in the signaling adapter MYD88 activate NF-kB and synergize with B cell receptor signaling in sustaining the survival of ABC DLBCL cells. In addition, inactivating mutations in a negative regulator of the NF-kB pathway, A20, occur almost exclusively in ABC DLBCL.

Indeed, genetic alterations affecting multiple components of the NF-κB signaling pathway have been recently identified in more than 50% of ABC-DLBCL patients, where these lesions promote constitutive NF-κB activation, thereby contributing to lymphoma growth. These include mutations of CARD11 (~10% of the cases), a lymphocyte-specific cytoplasmic scaffolding protein that—together with MALT1 and BCL10—forms the BCR signalosome, which relays signals from antigen receptors to the downstream mediators of NF-κB activation. An even larger fraction of cases (~30%) carry biallelic genetic lesions inactivating the negative NF-κB regulator A20. Further, high levels of expression of NF-κB target genes have been observed in ABC-DLBCL tumor samples.

Disclosed herein, in some embodiments, are methods of treating a DLBCL in an individual in need thereof, comprising administering to the individual a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. In some embodiments, the DLBCL is ABC-DLBCL.

In some embodiments, disclosed herein, are methods of treating a DLBCL in an individual in need thereof, comprising administering to the individual: (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; and (b) a BTK inhibitor. In some embodiments, the DLBCL is ABC-DLBCL.

In some embodiments, disclosed herein, are methods of treating a DLBCL in an individual in need thereof, comprising administering to the individual (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; and (b) irbutinib. In some embodiments, the DLBCL is ABC-DLBCL.

Follicular Lymphoma

As used herein, the term "follicular lymphoma" refers to any of several types of non-Hodgkin's lymphoma in which the lymphomatous cells are clustered into nodules or follicles. The term follicular is used because the cells tend to grow in a circular, or nodular, pattern in lymph nodes. The average age for people with this lymphoma is about 60. Follicular lymphoma, a B-cell lymphoma, is the most common indolent (slow-growing) form of NHL, accounting for approximately 20 percent to 30 percent of all NHLs.

CLL/SLL

Chronic lymphocytic leukemia and small lymphocytic lymphoma (CLL/SLL) are commonly thought as the same disease with slightly different manifestations. Where the cancerous cells gather determines whether it is called CLL or SLL. When the cancer cells are primarily found in the lymph nodes, it is called SLL. SLL accounts for about 5% to 10% of all lymphomas. When most of the cancer cells are in the bloodstream and the bone marrow, it is called CLL.

Both CLL and SLL are slow-growing diseases, although CLL, which is much more common, tends to grow slower. CLL and SLL are treated the same way. They are usually not considered curable with standard treatments, but depending on the stage and growth rate of the disease, most patients live longer than 10 years. Occasionally over time, these slow-growing lymphomas may transform into a more aggressive type of lymphoma.

Chronic lymphoid leukemia (CLL) is the most common type of leukemia. CLL is a lymphoid malignancy of clonal B cells that typically exhibit aberrant activation of the B-cell receptor (BCR) signaling pathway.

Small lymphocytic leukemia (SLL) is very similar to CLL described supra, and is also a cancer of B-cells. In SLL the abnormal lymphocytes mainly affect the lymph nodes. However, in CLL the abnormal cells mainly affect the blood and the bone marrow. The spleen may be affected in both conditions. SLL accounts for about 1 in 25 of all cases of non-Hodgkin lymphoma. It can occur at any time from young adulthood to old age, but is rare under the age of 50. SLL is considered an indolent lymphoma. This means that the disease progresses very slowly, and patients tend to live many years after diagnosis. However, most patients are diagnosed with advanced disease, and although SLL responds well to a variety of chemotherapy drugs, it is generally considered to be incurable. Although some cancers tend to occur more often in one gender or the other, cases and deaths due to SLL are evenly split between men and women. The average age at the time of diagnosis is 60 years.

Although SLL is indolent, it is persistently progressive. The usual pattern of this disease is one of high response rates to radiation therapy and/or chemotherapy, with a period of disease remission. This is followed months or years later by an inevitable relapse. Re-treatment leads to a response again, but again the disease will relapse. This means that although the short-term prognosis of SLL is quite good, over time, many patients develop fatal complications of recurrent disease. Considering the age of the individuals typically diagnosed with CLL and SLL, there is a need in the art for a simple and effective treatment of the disease with minimum side-effects that do not impede on the patient's quality of life. The instant invention fulfills this long standing need in the art.

Mantle Cell Lymphoma

As used herein, the term, "Mantle cell lymphoma" refers to a subtype of B-cell lymphoma, due to CD5 positive antigen-naive pregerminal center B-cell within the mantle zone that surrounds normal germinal center follicles. MCL cells generally over-express cyclin D1 due to a t(11:14) chromosomal translocation in the DNA. Men are affected most often. The average age of patients is in the early 60s. The lymphoma is usually widespread when it is diagnosed, involving lymph nodes, bone marrow, and, very often, the spleen. Mantle cell lymphoma is not a very fast growing lymphoma, but is difficult to treat.

Marginal Zone B-cell Lymphoma

As used herein, the term "marginal zone B-cell lymphoma" refers to a group of related B-cell neoplasms that involve the lymphoid tissues in the marginal zone, the patchy area outside the follicular mantle zone. Marginal zone lymphomas account for about 5% to 10% of lymphomas. The cells in these lymphomas look small under the microscope. There are 3 main types of marginal zone lymphomas including extranodal marginal zone B-cell lymphomas, nodal marginal zone B-cell lymphoma, and splenic marginal zone lymphoma.

MALT

The term "mucosa-associated lymphoid tissue (MALT) lymphoma", as used herein, refers to extranodal manifestations of marginal-zone lymphomas. Most MALT lymphoma are a low grade, although a minority either manifest initially as intermediate-grade non-Hodgkin lymphoma (NHL) or evolve from the low-grade form. Most of the MALT lymphoma occur in the stomach, and roughly 70% of gastric MALT lymphoma are associated with Helicobacter pylori infection. Several cytogenetic abnormalities have been identified, the most common being trisomy 3 or t(11;18). Many of these other MALT lymphoma have also been linked to infections with bacteria or viruses. The average age of patients with MALT lymphoma is about 60.

Nodal Marginal Zone B-Cell Lymphoma

The term "nodal marginal zone B-cell lymphoma" refers to an indolent B-cell lymphoma that is found mostly in the lymph nodes. The disease is rare and only accounts for 1% of all Non-Hodgkin's Lymphomas (NHL). It is most commonly diagnosed in older patients, with women more susceptible than men. The disease is classified as a marginal zone lymphoma because the mutation occurs in the marginal zone of the B-cells. Due to its confinement in the lymph nodes, this disease is also classified as nodal.

Splenic Marginal Zone B-Cell Lymphoma

The term "splenic marginal zone B-cell lymphoma" refers to specific low-grade small B-cell lymphoma that is incorporated in the World Health Organization classification. Characteristic features are splenomegaly, moderate lymphocytosis with villous morphology, intrasinusoidal pattern of involvement of various organs, especially bone marrow, and relative indolent course. Tumor progression with increase of blastic forms and aggressive behavior are observed in a minority of patients. Molecular and cytogenetic studies have shown heterogeneous results probably because of the lack of standardized diagnostic criteria.

Burkitt Lymphoma

The term "Burkitt lymphoma" refers to a type of Non-Hodgkin Lymphoma (NHL) that commonly affects children. It is a highly aggressive type of B-cell lymphoma that often starts and involves body parts other than lymph nodes. In spite of its fast-growing nature, Burkitt's lymphoma is often curable with modern intensive therapies. There are two broad types of Burkitt's lymphoma—the sporadic and the endemic varieties:

Endemic Burkitt's lymphoma: The disease involves children much more than adults, and is related to Epstein Barr Virus (EBV) infection in 95% cases. It occurs primarily is equatorial Africa, where about half of all childhood cancers are Burkitt's lymphoma. It characteristically has a high chance of involving the jawbone, a rather distinctive feature that is rare in sporadic Burkitt's. It also commonly involves the abdomen.

Sporadic Burkitt's lymphoma: The type of Burkitt's lymphoma that affects the rest of the world, including Europe and the Americas is the sporadic type. Here too, it's mainly a disease in children. The link between Epstein Barr Virus (EBV) is not as strong as with the endemic variety, though direct evidence of EBV infection is present in one out of five patients. More than the involvement of lymph nodes, it is the abdomen that is notably affected in more than 90% of the children. Bone marrow involvement is more common than in the sporadic variety.

Waldenstrom Macroglobnlinemia

The term "Waldenstrom macroglobulinemia", also known as lymphoplasmacytic lymphoma, is cancer involving a subtype of white blood cells called lymphocytes. It is characterized by an uncontrolled clonal proliferation of terminally differentiated B lymphocytes. It is also characterized by the lymphoma cells making an antibody called immunoglobulin M (IgM). The IgM antibodies circulate in the blood in large amounts, and cause the liquid part of the blood to thicken, like syrup. This can lead to decreased blood flow to many organs, which can cause problems with vision (because of poor circulation in blood vessels in the back of the eyes) and neurological problems (such as headache, dizziness, and confusion) caused by poor blood flow within the brain. Other symptoms can include feeling tired and weak, and a tendency to bleed easily. The underlying etiology is not fully understood but a number of risk factors have been identified, including the locus 6p21.3 on chromosome 6. There is a 2- to 3-fold risk increase of developing WM in people with a personal history of autoimmune diseases with autoantibodies and particularly elevated risks associated with hepatitis, human immunodeficiency virus, and rickettsiosis.

Multiple Myeloma

Multiple myeloma is a cancer of the white blood cells known as plasma cells. A type of B cell, plasma cells are a crucial part of the immune system responsible for the production of antibodies in humans and other vertebrates. They are produced in the bone marrow and are transported through the lymphatic system. When plasma cells become cancerous and grow out of control, they can produce a tumor called a plasmacytoma. These tumors generally develop in a bone, but they are also rarely found in other tissues. When a plasmacytoma starts in other tissues (such as the lungs or other organs), it is called an extramedullary plasmacytoma. An individual with only a single plasma cell tumor, has an isolated (or solitary) plasmacytoma. An individual with more than one plasmacytoma, has multiple myeloma.

Leukemia

Leukemia is a cancer of the blood or bone marrow characterized by an abnormal increase of blood cells, usually leukocytes (white blood cells). Leukemia is a broad term covering a spectrum of diseases. The first division is between its acute and chronic forms: (i) acute leukemia is characterized by the rapid increase of immature blood cells. This crowding makes the bone marrow unable to produce healthy blood cells. Immediate treatment is required in acute leukemia due to the rapid progression and accumulation of the malignant cells, which then spill over into the bloodstream and spread to other organs of the body. Acute forms of leukemia are the most common forms of leukemia in children; (ii) chronic leukemia is distinguished by the excessive build up of relatively mature, but still abnormal, white blood cells. Typically taking months or years to progress, the cells are produced at a much higher rate than normal cells, resulting in many abnormal white blood cells in the blood. Chronic leukemia mostly occurs in older people, but can theoretically occur in any age group. Additionally, the diseases are subdivided according to which kind of blood cell is affected. This split divides leukemias into lymphoblastic or lymphocytic leukemias and myeloid or myelogenous leukemias: (i) lymphoblastic or lymphocytic leukemias, the cancerous change takes place in a type of marrow cell that normally goes on to form lymphocytes, which are infection-fighting immune system cells; (ii) myeloid or myelogenous leukemias, the cancerous change takes place in a type of marrow cell that normally goes on to form red blood cells, some other types of white cells, and platelets.

Within these main categories, there are several subcategories including, but not limited to, acute lymphoblastic leukemia (ALL), acute myelogenous leukemia (AML), chronic myelogenous leukemia (CML), and chronic lymphoblastic leukemia (CLL).

AML

Acute myeloid leukemia (AML), also known as acute myelogenous leukemia, acute myeloblastic leukemia, acute granulocytic leukemia or acute nonlymphocytic leukemia, is a fast-growing form of cancer of the blood and bone marrow. Although overall AML is a relatively rare disease, it is the most common acute leukemia affecting adults. AML occurs when the bone marrow begins to make blasts, cells that have not yet completely matured. These blasts normally develop into white blood cells. However, in AML, these cells do not develop and are unable to ward off infections. In AML, the bone marrow may also make abnormal red blood cells and platelets. The number of these abnormal cells increases rapidly, and the abnormal (leukemia) cells begin to crowd out the normal white blood cells, red blood cells and platelets that the body needs.

One of the main factors that differentiate AML from the other main forms of leukemia is that it has eight different subtypes, which are based on the cell that the leukemia developed from. The types of acute myelogenous leukemia include: Myeloblastic (M0)—on special analysis; Myeloblastic (M1)—without maturation; Myeloblastic (M2)—with maturation; Promyeloctic (M3); Myelomonocytic (M4); Monocytic (M5); Erythroleukemia (M6); and Megakaryocytic (M7). In vitro studies have shown that bone marrow mesenchymal stromal cells (BM-MSC) protect AML blasts from spontaneous and chemotherapy-induced apoptosis (A. M. Abdul-Azizm et al Cancer Res (2017) 77(2): 303-311). Abdul-Azizm et al report that macrophage inhibitory factor (MIF)-induced stromal PKCβ/IL8 is the essential feature of this stromal support in human AML. The authors demonstrate that pharmacologic inhibition of PKCβ inhibits MIF-induced IL8 induction in BM-MSCs. These results show that a bidirectional, prosurvival mechanism between AML blasts and BM-MSCs exists and that this mechanism is blocked by inhibition of PKCβ.

Bcl2 is a cellular oncogene product associated with the t(14,18) translocation commonly seen in B-cell lymphomas. However, Bcl2 expression levels alone do not always correlate with poor prognosis in patients diagnosed with AML. The phosphorylation status of Bcl2 can influence Bcl2 activity. PKCα and extracellular signal-related kinase (ERK) have been identified as Bcl2 kinases that promote survival. It has also been demonstrated that Bcl2 is phosphorylated in nearly half the patient AML blast cells tested. Furthermore, Bcl2 was always phosphorylated in AML blast cells with activated PKCα and ERK but never in cells that lack both activated kinases. AML patients with blast cells expressing phosphorylated Bcl2 exhibit shorter overall survival (particularly when PKCα was active) compared to patients with blast cells expressing unphosphorylated Bcl2. Survival of AML patients with active PKCα, was shorter compared to patients with no phosphorylated PKC and appeared to be shortest in patients in which PKCα and BCL2 were phosphorylated. Patients with upregulated activation of BCL2 and in PKCα tytpically demonstrate the poorest climinal outcomes. It has been shown that the PKC inhibitor enzastaurin promotes the apoptosis of AML derived cell lines and in blast cells derived from patients with newly diagnosed or recurrent AML. This effect was not due to inhibition of PKCβ, but rather was correlated with PKCα inhibition.

Described herein, in some embodiments, are methods of treating an AML in a subject in need thereof comprising administering to the individual a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. In some embodiments, the method further comprises administration of a BLC2 inhibitor.

It has been demonstrated that PKCβ inhibition may play an important role in myeloid malignancies as well as PKCα. Li, et al (Leukemia & Lymphoma (2011), 52(7):1312-1320) shows that PKCβ signaling is upregulated in the human CML cell line K562 and that inhibition of PKCβ inhibited K562 cell proliferation in a time- and dose-dependent manner. Because the PKCβ inhibitor (a novel bisindolymaleimide derivative WK234) retarded cell proliferation and induced apoptosis through suppression of the PKCβ signal pathway, inhibition of PKCβ might be a promising approach for the treatment of CML. Further, Dufies, et al (Oncotarget 2011; 2: 874-885) provides supporting evidence that AXL upregulation is responsible for resistance of CML cells to imatinib and is a hallmark of imatinib resistance. The authors demonstrate that this upregulation of AXL requires both PKCα and PKCβ. Thus, inhibition of both PKCα and PKCβ could be a possible mechanism for treatment of patients with imatinib resistant CML.

In research related to acute lymphoblastic leukemia (ALL), Saba, et al (Leukemia & Lymphoma, 2011; 52(5): 877-886) found that PKCβ inhibitor treatment resulted in a dose-dependent reduction in viability in all five ALL cell lines tested.

Described herein, in some embodiments, is a method of treating leukemia in a subject in need thereof comprising administering to the individual a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, wherein the leukemia is chosen from acute lymphoblastic leukemia (ALL), acute myelogenous leukemia (AML), chronic myelogenous leukemia (CML), or chronic lymphoblastic leukemia (CLL).

T-cell Lymphomas

T-cell lymphomas make up less than 15% of non-Hodgkin lymphomas in the United States. There are many types of T-cell lymphoma, but they are all fairly rare.

Precursor T-Lymphoblastic Lymphoma/Leukemia

Precursor T-Lymphoblastic Lymphoma/Leukemia accounts for about 1% of all lymphomas. It can be considered either a lymphoma or leukemia, depending on how much of the bone marrow is involved (leukemias have more bone marrow involvement). The cancer cells are small-to-medium sized, immature T-cells.

Precursor T-lymphoblastic lymphoma often starts in the thymus, where many T cells are made. Patients are most often young adults, with males being affected more often than females. Precursor T-lymphoblastic lymphoma is fast-growing, but the prognosis folllowgin chemotherapy treatment is good if the cancer has not spread to the bone marrow. The lymphoma form of this disease is often treated in the same way as the leukemia form.

Peripheral T-cell Lymphomas

Peripheral T-cell lymphomas (PTCLs) are uncommon and aggressive types of non-Hodgkin lymphoma (NHL) that develop in mature white blood cells. PTCLs generally affect people aged 60 years and older and are diagnosed slightly more often in men than in women.

Cutaneous T-cell lymphomas (mycosis fungoides, Sezary syndrome, and others) start in the skin. Skin lymphomas account for about 5% of all lymphomas.

Adult T-cell lymphoblastic leukemia/lymphoma is typically caused by infection with a virus called HTLV-1. This disease is rare in the United States and much more common in Japan, the Caribbean, and parts of Africa—where the HTLV-1 virus is more common. There are 4 subtypes: smoldering, chronic, acute, and lymphoma.

The smoldering subtype has abnormal T-cells in the blood without an increased number of lymphocytes in the blood. This lymphoma may involve the skin or lungs, but there is no involvement of other tissues. The smoldering type grows slowly and has a good prognosis.

The chronic subtype also grows slowly and has a good prognosis. It has an increase in total lymphocytes and T-cells in the blood. It may involve the skin, lungs, lymph nodes, liver, and/or spleen, but nor other tissues.

The acute subtype acts like acute leukemia. It has high lymphocyte and T-cell counts, often along with enlargement of lymph nodes, liver, and spleen. The skin and other organs may be involved with lymphoma as well. Patients often have fever, night sweats, and/or weight loss, as well as certain abnormal blood test results.

The lymphoma subtype grows more quickly than the chronic and smoldering types, but not as fast as the acute type. It has enlarged lymph nodes without increased lymphocytes in the blood, and the T-cell count is not high.

Angioimmunoblastic T-cell lymphoma (AITL accounts for between 1-2 percent of all cases of NHL and typically follows an aggressive course. AITL is more common in older adults. AITL tends to involve the lymph nodes as well as the spleen or liver, which can cause them to be enlarged. Patients usually have fever, weight loss, and skin rashes and often develop infections. This lymphoma often progresses quickly. Treatment is often effective at first, but the lymphoma tends to relapse.

Extranodal, nasal natural killer/T-cell lymphoma is a rare lymphoma that often involves the upper airway passages, such as the nose and upper throat, but it can also invade the skin and digestive tract. Cells of this lymphoma are similar in some ways to normal natural killer (NK) cells. NK cells are lymphocytes that can respond to infections more quickly than T-cells and B-cells. Extranodal, nasal NK/T-cell lymphoma is more commonly found in Asia and Latin America and is associated with the Epstein-Barr virus (EBV).

Enteropathy-associated intestinal T-cell lymphoma (EATL): EATL is a lymphoma that occurs in the lining of the intestine. This lymphoma is most common in the jejunum (the second part of the small intestine), but can also occur elsewhere in the small intestine and in the colon. EATL often affects more than one place in the intestine, and may spread to the nearby lymph nodes, as well. It can cause the intestine to become obstructed or perforated. There are two subtypes of this lymphoma.

Type I EATL occurs in people with a disease called gluten-sensitive enteropathy (also known as celiac disease, celiac sprue, or sprue). Sprue is an autoimmune disease in which gluten, the main protein in wheat flour, causes the body produce antibodies that attack the lining of the intestine and other parts of the body. This lymphoma is more common in men than women, and tends to occur in people in their 60s and 70s. People who do not tolerate gluten, but don't have sprue, do not seem to have an increased risk of this type of lymphoma. Type II EATL is not linked to sprue and is less common than type I.

Anaplastic large cell lymphoma (ALCL) is a rare T-cell lymphoma that constitutes about 3 percent of all cases of lymphomas in adults. ALCL is much more prevalent in children. ALCL usually starts in lymph nodes and can also spread to skin. This type of lymphoma tends to be fast-growing, but many people with this lymphoma are cured with aggressive chemotherapy.

The two main forms of ALCL are primary cutaneous, which only affects the skin, and systemic. Systemic ALCL is divided into subtypes based upon the presence or absence of anaplastic lymphoma kinase (ALK). ALK-positive ALCL tends to occur in younger patients and tends to have a better prognosis than the ALK-negative type.

Peripheral T-cell lymphoma, not otherwise unspecified is the most common type of PTCL and is the name given to T-cell lymphomas that don't readily fit into any of the groups above. They make up about half of all T-cell lymphomas. Most people diagnosed with this disease are in their 60s. This lymphoma often has nodal involvement, but extranodal sites, such as the liver, bone marrow, gastrointestinal tract and skin, may also be involved. As a group, these lymphomas tend to be widespread and grow quickly. Some patients respond well to chemotherapy, but long-term survival is not common.

Ewing's Sarcoma

Ewing's sarcoma is a cancerous tumor that grows in the bones or in the tissue around bones (soft tissue), typically the legs, pelvis, ribs, arms or spine. Ewing sarcoma can spread to the lungs, bones and bone marrow. Ewing sarcoma is the second most frequent childhood bone tumor, but it is very rare. Ewing sarcoma is a highly metastatic tumor with around 25% of patients presenting metastasis at the time of diagnosis. About half of all Ewing sarcoma tumors occur in children and young adults between ages 10 and 20. Although not often seen, Ewing sarcoma can occur as a second cancer, especially in patients treated with radiation therapy.

The most common translocation in Ewing's Sarcoma, present in about 90% of cases, generates an aberrant transcription factor through fusion of the EWSR1 gene with the FLI1 gene. PKCβ has been found to be a target modulated by EWSR1-FLI1 in primary Ewing tumors compared with other tumors types. PKCβ has been demonstrated to be crucial for Ewing's Sarcoma tumor cell survival in vitro and tumor development in vivo.

Described herein, in some embodiments, are methods of treating a Ewing's Sarcoma in a subject in need thereof comprising administering to the individual a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof.

BTK Inhibitors

The Bruton's tyrosine kinase (BTK) inhibitor ibrutinib is an FDA approved anticancer drug targeting B-cell malignancies. Other BTK inhibitors currently in some stage of clinical development include, but are not limited to: ONO/GS-4059 (Ono Pharmaceuticals/Gilead Sciences), AVL-292/CC-292/spebrutinib (Celgene Corporation), BGB-3111 (BeiGene), and ACP-196/acalabrutinib (Acerta Pharma), M7583 (EMD Serono/Merck KGaA), MSC2364447C(EMD Serono/Merck KGaA), BIIB068 (Biogen), AC0058TA (ACEA Biosciences), and DTRMWXHS-12 (Zhejiang DTRM Biopharma).

Methods of Treatment

Hematological Malignancy

One embodiment provides a method of treating a hematological malignancy in a subject in need thereof comprising administering to the subject a composition comprising a compound, or a pharmaceutically acceptable salt thereof, selected from the group consisting of:

$N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N2— ethyl — 5-fluoropyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2$,$N^2$-dimethylpyrimidine-2,4-diamine, $N^2$-cyclopropyl-N4-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoropyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2$-methylpyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2$-isopropylpyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-$N^2$-ethylpyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-$N^2$,$N^2$-dimethylpyrimidine-2,4-diamine, 5-{[(8S)-6,8-dimethyl-6,9-diazaspiro[4.5]dec-9-yl]carbonyl}-N-(5-fluoro-2-methylpyrimidin-4-yl)-6,6-dimethyl-1,4,5,6-tetrahydropyrrolo[3,4-c]pyrazol-3-amine, $N^4$-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-$N^2$-ethyl-5-fluoropyrimidine-2,4-diamine, $N^4$-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-$N^2$-ethyl-5-fluoropyrimidine-2,4-diamine, $N^2$-ethyl-5-fluoro-$N^4$-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)pyrimidine-2,4-diamine, $N^4$-(6,6-dimethyl-5-{[(2S,5R)-2,4,5-trimethylpiperazin-1-yl]carbonyl}-1,4,5,6-tetrahydropyrrolo[3,4-c]pyrazol-3-yl)-$N^2$-ethyl-5-fluoropyrimidine-2,4-diamine, 4-[(6,6-dimethyl-5-{[(2S,5R)-2,4,5-trimethylpiperazin-1-yl]carbonyl}-1,4,5,6-tetrahydropyrrolo[3,4-c]pyrazol-3-yl)amino]pyrimidine-2-carbonitrile, N-(2-ethyl-5-fluoropyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine, N-(2-ethyl-5-fluoropyrimidin-4-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, 2-((5S)-4-{[3-[(2-ethyl-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, N-(5-fluoro-2-methylpyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine, N-(5-fluoro-2-propylpyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine, N-(5-fluoro-2-isopropylpyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine, N-[5-fluoro-2-(methoxymethyl)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-N-(4-methoxypyrimidin-2-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-6,6-dimethyl-N-(4-methylpyrimidin-2-yl)-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-6,6-dimethyl-N-[4-(trifluoromethyl)pyrimidin-2-yl]-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-6,6-dimethyl-N-(4-methylpyrimidin-2-yl)-1,4,5,6-tetrahydropyrrolo[3,4-c]pyrazol-3-amine, N-(2-ethoxy-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine, N-(2-ethoxy-5-fluoropyrimidin-4-yl)-6,6-dimethyl-5-{[4-ethyl (2S,5R)-2,5-dimethylpiperazin-1-yl]carbonyl}-1,4,5,6-tetrahydropyrrolo[3,4-c]pyrazol-3-amine, N-(2-ethoxy-5-fluoropyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine, N-(2-ethoxy-5-fluoropyrimidin-4-yl)-5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-amine, N-(2-ethoxy-5-fluoropyrimidin-4-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, N-[5-fluoro-2-(2,2,2-trifluoroethoxy)pyrimidin-4-yl]-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, N-[5-fluoro-2-(2,2,2-trifluoroethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine, N-[5-fluoro-2-(2,2,2-trifluoroethoxy)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, 2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 5-[(4-fluoro-1-methylpiperidin-4-yl)carbonyl]-N-[5-fluoro-2-(2,2,2-trifluoroethoxy)pyrimidin-4-yl]-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-[5-fluoro-2-(methoxymethyl)pyrimidin-4-yl]-6,6-dimethyl-1,4,5,6-tetrahydropyrrolo[3,4-c]pyrazol-3-amine, and 2-((5S)-4-{[3-{[5-fluoro-2-(methoxymethyl)pyrimidin-4-yl]amino}-6,6-dimethyl-4,6-dihydropyrrolo[3,4-c]pyrazol-5(1H)-yl]carbonyl}-1,5-dimethylpiperazin-2-yl)ethanol.

Another embodiment provides the method of treating a hematological malignancy, wherein the compound is $N^4$-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-$N^2$-ethyl-5-fluoropyrimidine-2,4-diamine, or a pharmaceutically acceptable salt thereof. Another embodiment provides the method of treating a hematological malignancy, wherein the compound is $N^4$-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-$N^2$-ethyl-5-fluoropyrimidine-2,4-diamine, or a pharmaceutically acceptable salt thereof. Another embodiment provides the method of treating a hematological malignancy, wherein the compound is 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating a hematological malignancy, wherein the compound is 5-{[(2S,5R)-2,5-dimethyl-4-(tetrahydro-2H-pyran-4-ylmethyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating a hematological malignancy, wherein the compound is 5-{[(2S,5R)-2,5-dimethyl-4-(tetrahydro-2H-pyran-4-yl)piperazin-1-yl]carbonyl}-N-(4-methoxypyrimidin-2-yl)-6,6-dimethyl-1,4,5,6-tetrahydropyrrolo[3,4-c]pyrazol-3-amine, or a pharmaceutically acceptable salt thereof. Another embodiment provides the method of treating a hematological malignancy, wherein the compound is 5-{[(2S,5R)-2,5-dimethyl-4-(tetrahydro-2H-pyran-4-yl)piperazin-1-yl]carbonyl}-6,6-dimethyl-N-[4-(trifluoromethyppyrimidin-2-yl]-1,4,5,6-tetrahydropyrrolo[3,4-c]pyrazol-3-amine, or a pharmaceutically acceptable salt thereof. Another embodiment provides the method of treating a hematological malignancy, wherein the compound is 5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating a hematological malignancy, wherein the compound is $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N2-ethyl-5-fluoropyrimidine-2,4-diamine, or a pharmaceutically acceptable salt thereof. Another embodiment provides the method of treating a hematological malignancy, wherein the compound is $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-$N^2$-ethylpyrimidine-2,4-diamine, or a pharmaceutically acceptable salt thereof. Another embodiment provides the method of treating a hematological malignancy, wherein the hematological malignancy is a lymphoma or leukemia. Another embodiment provides the method of treating a diffuse large B-cell lymphoma (DLBCL) or chronic lymphocytic leukemia (CLL).

One embodiment provides a method of treating a hematological malignancy in a subject in need thereof comprising administering to the subject a composition comprising a compound having the formula 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and a pharmaceutically acceptable excipient.

One embodiment provides a method of treating a hematological malignancy in a subject in need thereof comprising administering to the subject a composition comprising a compound, or a pharmaceutically acceptable salt thereof, selected from the group consisting of:

$N^2$-(cyclopropylmethyl)-$N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoropyrimidine-2,4-diamine;

$N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2$-isobutylpyrimidine-2,4-diamine;

5-{[(2S,5R)-4-ethyl-2,5-dimethylpiperazin-1-yl]carbonyl}-N-(5-fluoro-2-methoxypyrimidin-4-yl)-6,6-dimethyl-1,4,5,6-tetrahydropyrrolo[3,4-c]pyrazol-3-amine;

5-{[(2S,5R)-4-ethyl-2,5-dimethylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

5-{[(2S,5R)-4-ethyl-2,5-dimethylpiperazin-1-yl]carbonyl}-N-(5-fluoro-2,6-dimethylpyrimidin-4-yl)-6,6-dimethyl-1,4,5,6-tetrahydropyrrolo[3,4-c]pyrazol-3-amine;

2(S),5(S)-{[dimethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

[3-(5-fluoro-2-methyl-pyrimidin-4-ylamino)-6,6-dimethyl-4,6-dihydro-1H-pyrrolo[3,4-c]pyrazol-5-yl]-[4-(3-hydroxy-propyl)-2,5-dimethyl-piperazin-1-yl]-methanone;

$N^4$-(6,6-dimethyl-5-{[(3 S,8 aS)-3-methylhexahydropyrrolo[1,2-a]pyrazin-2(1H)-yl]carbonyl}-1,4,5,6-tetrahydropyrrolo[3,4-c]pyrazol-3-yl)-$N^2$-ethyl-5-fluoropyrimidine-2,4-diamine;

$N^2$-ethyl-5-fluoro-$N^4$-(5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-yl)pyrimidine-2,4-diamine;

N4-(5-{[(2S,5R)-2,5-dimethyl-4-(3,3,3-trifluoropropyl)piperazin-1-yl]carbonyl}-6,6-dimethyl-1,4,5,6-tetrahydropyrrolo[3,4-c]pyrazol-3-yl)-N2-ethyl-5-fluoropyrimidine-2,4-diamine;

N-(5-fluoro-2-morpholin-4-ylpyrimidin-4-yl)-6,6-dimethyl-5{[(2S,5R)-2,4,5-trimethylpiperazin-1-yl]carbonyl}-1,4,5,6-tetrahydropyrrolo[3,4-c]pyrazol-3-amine;

$N^2$-ethyl-5-fluoro-$N^4$-{5-[(4-fluoro-1-methylpiperidin-4-yl)carbonyl]-6,6-dimethyl-1,4,5,6-tetrahydropyrrolo[3,4-c]pyrazol-3-yl}pyrimidine-2,4-diamine;

N-(2-ethyl-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine;

N-(2-ethoxypyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine;

5-{[(2S,5R)-2,5-dimethyl-4-(3,3,3-trifluoropropyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine;

5-[(4-fluoro-1-methylpiperidin-4-yl)carbonyl]-N-(5-fluoro-2-methylpyrimidin-4-yl)-6,6-dimethyl-1,4,5,6-tetrahydropyrrolo[3,4-c]pyrazol-3-amine;

N-(2-ethyl-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine;

N-(5-fluoro-2-methylpyrimidin-4-yl)-6,6-dimethyl-5-{[(3S,8aS)-3-methylhexahydropyrrolo[1,2-a]pyrazin-2(1H)-yl]carbonyl}-1,4,5,6-tetrahydropyrrolo[3,4-c]pyrazol-3-amine;

N-(5-fluoro-2-methylpyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine;

5-{[(3S)-3-ethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

5-{[(3R)-3-ethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

5-{[(2S,5R)-2,5-dimethyl-4-(tetrahydro-2H-pyran-4-yl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

4-[((2R,5S)-4-{[3-[(5-fluoro-2-methylpyrimidin-4-yl)amino]-6,6-dimethyl-4,6-dihydropyrrolo[3,4-c]pyrazol-5(1H)-yl]carbonyl}-2,5-dimethylpiperazin-1-yl)methyl]tetrahydro-2H-pyran-4-ol;

2-((5S)-4-{[3-[(5-fluoro-2-methylpyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

2-((5S)-4-{[3-[(5-fluoro-2-methylpyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

5-{[(2S,5R)-2,5-dimethyl-4-(tetrahydro-2H-pyran-4-ylmethyl)piperazin-1-yl]carbonyl}-N-(4-methoxypyrimidin-2-yl)-6,6-dimethyl-1,4,5,6-tetrahydropyrrolo[3,4-c]pyrazol-3-amine;

N-(4,6-dimethylpyrimidin-2-yl)-5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-amine;

N-[5-fluoro-2-(3-methoxypropoxy)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine;

N-[5-fluoro-2-(3-methoxypropoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine;

N-[5-fluoro-2-(2-methoxyethoxy)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine;

N-[5-fluoro-2-(2-methoxyethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine;

2(S),5(S)-{[dimethyl-4-methylpiperazin-1-yl]carbonyl}-N-(5-fluoro-2-ethoxypyrimidin-4-yl)-6,6-dimethyl-1,4,5,6-tetrahydropyrrolo[3,4-c]pyrazol-3-amine;

[3-(2-Ethoxy-5-fluoro-pyrimidin-4yl-amino)-6,6-dimethyl-4,6-dihydro-1H-pyrrolo[3,4-c]pyrazol-5-yl]-(R)-hexahydro-pyrrolo[1,2-a]pyrazin-2-yl-methanone;

5-{[(3S,8 aS)-3,8a-dimethylhexahydropyrrolo[1,2-a]pyrazin-2(1H)-yl]carbonyl}-N-(2-ethoxy-5-fluoropyrimidin-4-yl)-6,6-dimethyl-1,4,5,6-tetrahydropyrrolo[3,4-c]pyrazol-3-amine;

5-{[(3S)-3,4-dimethylpiperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine;

5-{[(3R)-3,4-dimethylpiperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine;

5-{[(2S,5R)-2,5-dimethyl-4-(3,3,3-trifluoropropyl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine;

N-(2-ethoxy-5-fluoropyrimidin-4-yl)-5-{[(3S,8aS)-3-isopropylhexahydropyrrolo[1,2-a]pyrazin-2(1H)-yl]carbonyl}-6,6-dimethyl-1,4,5,6-tetrahydropyrrolo[3,4-c]pyrazol-3-amine;

4-[((2R,5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-2,5-dimethylpiperazin-1-yl)methyl]tetrahydro-2H-pyran-4-ol;

2-((5S)-4-{[3-[(5-fluoro-2-methoxypyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

2-((5S)-4-{[3-[(5-fluoro-2-methoxypyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

N-(2-ethoxy-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine;

N-[5-fluoro-2-(2-methoxyethoxy)pyrimidin-4-yl]-5-[(4-fluoro-1-methylpiperidin-4-yl)carbonyl]-6,6-dimethyl-1,4,5,6-tetrahydropyrrolo[3,4-c]pyrazol-3-amine;

N-[5-fluoro-2-(3-methoxypropoxy)pyrimidin-4-yl]-5-[(4-fluoro-1-methylpiperidin-4-yl)carbonyl]-6,6-dimethyl-1,4,5,6-tetrahydropyrrolo[3,4-c]pyrazol-3-amine;

N-(2-ethoxy-5-fluoropyrimidin-4-yl)-6,6-dimethyl-5-{[1-(3,3,3-trifluoropropyl)piperidin-4-yl]carbonyl}-1,4,5,6-tetrahydropyrrolo[3,4-c]pyrazol-3-amine;

N-(2-ethoxy-5-fluoropyrimidin-4-yl)-6,6-dimethyl-5-{[1-(tetrahydro-2H-pyran-4-yl)piperidin-4-yl]carbonyl}-1,4,5,6-tetrahydropyrrolo[3,4-c]pyrazol-3-amine;

N-(4-ethoxypyrimidin-2-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine;

N-(4-ethoxypyrimidin-2-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine; or 2-((5S)-4-{[3-{[5-fluoro-2-(methoxymethyl)pyrimidin-4-yl]amino}-6,6-dimethyl-4,6-dihydropyrrolo[3,4-c]pyrazol-5(1H)-yl]carbonyl}-1,5-dimethylpiperazin-2-yl)ethanol.

Another embodiment provides the method of treating a hematological malignancy, wherein the compound is N-(4-ethoxypyrimidin-2-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine, or a pharmaceutically acceptable salt thereof. Another embodiment provides the method of treating a hematological malignancy, wherein the compound is 5-{[(3S,8aS)-3,8a-dimethylhexahydropyrrolo[1,2-a]pyrazin-2(1H)-yl]carbonyl}-N-(2-ethoxy-5-fluoropyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating a hematological malignancy, wherein the compound is N-(4,6-dimethylpyrimidin-2-yl)-5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-amine, or a pharmaceutically acceptable salt thereof. Another embodiment provides the method of treating a hematological malignancy, wherein the compound is N-[5-fluoro-2-(3-methoxypropoxy)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine, or a pharmaceutically acceptable salt thereof. Another embodiment provides the method of treating a hematological malignancy, wherein the compound is N-(2-ethoxypyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine, or a pharmaceutically acceptable salt thereof. Another embodiment provides the method of treating a hematological malignancy, wherein the compound is N-(2-ethyl-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine, or a pharmaceutically acceptable salt thereof. Another embodiment provides the method of treating a hematological malignancy, wherein the compound is $N^2$-ethyl-5-fluoro-$N^4$-(5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-yl)pyrimidine-2,4-diamine, or a pharmaceutically acceptable salt thereof. Another embodiment provides the method of treating a hematological malignancy, wherein the compound is 5-{[(2S,5R)-2,5-dimethyl-4-(tetrahydro-2H-pyran-4-yl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating a hematological malignancy, wherein the compound is 5-{[(2S,5R)-4-ethyl-2,5-dimethylpiperazin-1-yl]carbonyl}-N-(5-fluoro-2,6-dimethylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating a hematological malignancy, wherein the compound is N-(2-ethoxy-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine, or a pharmaceutically acceptable salt thereof. Another embodiment provides the method of treating a hematological malignancy, wherein the compound is 4-[((2R,5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-2,5-dimethylpiperazin-1-yl)methyl]tetrahydro-2H-pyran-4-ol, or a pharmaceutically acceptable salt thereof. Another embodiment provides the method of treating a hematological malignancy, wherein the compound is N-[5-fluoro-2-(2-methoxyethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine, or a pharmaceutically acceptable salt thereof. Another embodiment provides the method of treating a hematological malignancy, wherein the compound is 5-{[(2S,5R)-2,5-dimethyl-4-(tetrahydro-2H-pyran-4-ylmethyl)piperazin-1-yl]carbonyl}-N-(4-methoxypyrimidin-2-yl)-6,6-dimethyl-1,4,5,6-tetrahydropyrrolo[3,4-c]pyrazol-3-amine, or a pharmaceutically acceptable salt thereof. Another embodiment provides the method of treating a hematological malignancy, wherein the compound is N-(5-fluoro-2-methylpyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine, or a pharmaceutically acceptable salt thereof. Another embodiment provides the method of treating a hematological malignancy, wherein the compound is $N^2$-(cyclopropylmethyl)-$N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoropyrimidine-2,4-diamine, or a pharmaceutically acceptable salt thereof.

One embodiment provides a method of treating a hematological malignancy in a subject in need thereof comprising administering to the subject a composition comprising a compound, or a pharmaceutically acceptable salt thereof, selected from the group consisting of:

N-(5-{[(8S)-6,8-dimethyl-6,9-diazaspiro[4.5]dec-9-yl]carbonyl}-6,6-dimethyl-1,4,5,6-tetrahydropyrrolo[3,4-c]pyrazol-3-yl)pyridine-2-carboxamide;

N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)benzamide;

N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)-3-methoxybenzamide;

3,4-dichloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)benzamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-4,6-dimethylpicolinamide;

N-(5-((3S,8a S)-3-(cyclohexylmethyl)-octahydropyrrolo[1,2-a]pyrazine-2-carbonyl)-6,6-dimethyl-1,4,5,6-tetrahydropyrrolo[3,4-c]pyrazol-3-yl)picolinamide;

3-cyano-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)benzamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2,3-dihydrobenzofuran-5-carboxamide;

4,5-dichloro-N-(6,6-dimethyl-5-(3S,8aS)-3-methyl-octahydropyrrolo[1,2-a]pyrazine-2-carbonyl)-1,4,5,6-tetrahydropyrrolo[3,4-c]pyrazol-3-yl)thiazole-2-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)H-pyrrolo[1,2-f]pyrimidine-3-carboxamide;

N-(5-((2R,5S)-2-(2-hydroxyethyl)-5-methyl-1-propylpiperazine-4-carbonyl)-6,6-dimethyl-1,4,5,6-tetrahydropyrrolo[3,4-c]pyrazol-3-yl)picolinamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-nitropicolinamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)quinoline-2-carboxamide;

N-(5-((+/−)-trans-1-allyl-2,5-dimethylpiperazine-4-carbonyl)-6,6-dimethyl-1,4,5,6-tetrahydropyrrolo[3,4-c]pyrazol-3-yl)picolinamide;

5-bromo-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)picolinamide, N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-fluoropicolinamide;

N-(5-((+/−)-trans-1-ethyl-2,5-dimethylpiperazine-4-carbonyl)-6,6-dimethyl-1,4,5,6-tetrahydropyrrolo[3,4-c]pyrazol-3-yl)picolinamide;

N-(5-((+/−)-trans-1-(cyclopropylmethyl)-2,5-dimethylpiperazine-4-carbonyl)-6,6-dimethyl-1,4,5,6-tetrahydropyrrolo[3,4-c]pyrazol-3-yl)picolinamide;

N-(5-(1-(3-hydroxypropyl)-2,5-dimethylpiperazine-4-carbonyl)-6,6-dimethyl-1,4,5,6-tetrahydropyrrolo[3,4-c]pyrazol-3-yl)picolinamide;

N-(5-((3S,8aS)-3-isopropyl-octahydropyrrolo[1,2-a]pyrazine-2-carbonyl)-6,6-dimethyl-1,4,5,6-tetrahydropyrrolo[3,4-c]pyrazol-3-yl)picolinamide;

2-bromo-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)thiazole-4-carboxamide;

N-(6,6-dimethyl-5-((2R,5S)-1,2,5-trimethylpiperazine-4-carbonyl)-1,4,5,6-tetrahydropyrrolo[3,4-c]pyrazol-3-yl)picolinamide;

N-(5-((2R,5S)-1-ethyl-2,5-dimethylpiperazine-4-carbonyl)-6,6-dimethyl-1,4,5,6-tetrahydropyrrolo[3,4-c]pyrazol-3-yl)picolinamide;

N-(5-((2R,5S)-2,5-dimethyl-1-propylpiperazine-4-carbonyl)-6,6-dimethyl-1,4,5,6-tetrahydropyrrolo[3,4-c]pyrazol-3-yl)picolinamide;

N-(5-((2R,5S)-1-(cyclopropylmethyl)-2,5-dimethylpiperazine-4-carbonyl)-6,6-dimethyl-1,4,5,6-tetrahydropyrrolo[3,4-c]pyrazol-3-yl)picolinamide;

N-(5-((2R,5S)-1-butyl-2,5-dimethylpiperazine-4-carbonyl)-6,6-dimethyl-1,4,5,6-tetrahydropyrrolo[3,4-c]pyrazol-3-yl)picolinamide;

N-(6,6-dimethyl-5-{[(2S)-2,4,5,5-tetramethylpiperazin-1-yl]carbonyl}-1,4,5,6-tetrahydropyrrolo[3,4-c]pyrazol-3-yl)pyridine-2-carboxamide;

N-(5-{[(7S)-5,7-dimethyl-5,8-diazaspiro[3.5]non-8-yl]carbonyl}-6,6-dimethyl-1,4,5,6-tetrahydropyrrolo[3,4-c]pyrazol-3-yl)pyridine-2-carboxamide;

N-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)pyridine-2-carboxamide;

N-(5-((2R,5S)-2,5-dimethyl-1-(2(tetradhydro-2H-pyran-4-ypethyl)piperazine-4-carbonyl)-6,6-dimethyl-1,4,5,6-tetrahydropyrrolo[3,4-c]pyrazol-3-yl)picolinamide;

N-(5-((2R,5S)-2,5-dimethyl-1-(tetrahydro-2H-pyran-4-yl)piperazine-4-carbonyl)-6,6-dimethyl-1,4,5,6-tetrahydropyrrolo[3,4-c]pyrazol-3-yl)picolinamide;

N-(5-{[(2S,5R)-2,5-dimethyl-4-(tetrahydrofuran-3-ylmethyl)piperazin-1-yl]carbonyl}-6,6-dimethyl-1,4,5,6-tetrahydropyrrolo[3,4-c]pyrazol-3-yl)pyridine-2-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)isoquinoline-3-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1,6-naphthyridine-2-carboxamide;

3-cyclopropyl-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1H-pyrazole-5-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)quinoxaline-2-carboxamide;

3-tert-butyl-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1-methyl-1H-pyrazole-5-carboxamide;

3-cyclopropyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1H-pyrazole-5-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-fluoropyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-methoxypyridine-2-carboxamide;

5-chloro-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)pyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-6-methylpyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-ethyl-1-methyl-1H-pyrazole-5-carboxamide;

2-cyclopropyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1,3-oxazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-methylbenzamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-4-fluorobenzamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-fluorobenzamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-ethylpyridine-2-carboxamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-methylpyridine-2-carboxamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-methoxypyridine-2-carboxamide;

5-chloro-N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)pyridine-2-carboxamide;

2-(3,5-dimethylisoxazol-4-yl)-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)acetamide;

5-cyano-N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)pyridine-2-carboxamide; and 5-cyano-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)pyridine-2-carboxamide.

One embodiment provides a method of treating a hematological malignancy in a subject in need thereof comprising administering to the subject a composition comprising a compound, or a pharmaceutically acceptable salt thereof, having the formula (I):

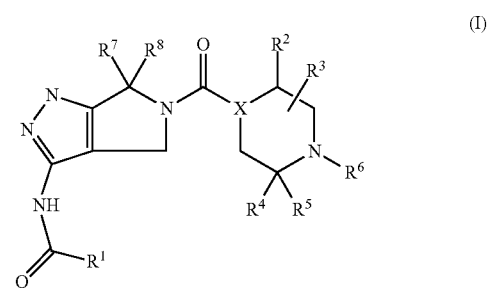

(I)

wherein:
X is C or N;
$R^1$ is selected from an aryl or

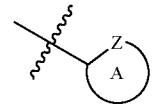

wherein ring A is a 5 to 6 membered heterocyclyl containing Z, wherein Z is an O, S or N heteroatom which is adjacent to the point of attachment, and wherein $R^1$ is optionally further substituted with 0 to 3 $R^9$ groups and wherein two of the $R^9$ groups may optionally cyclize to form an aryl or a 5-6 membered heterocyclyl ring containing N or S fused to the aryl or heterocyclyl to which it is attached;

$R^2$ is H or $C_1$-$C_6$ alkyl optionally further substituted with 0 to 3 $R^9$ groups;

when X is N, $R^3$ may be attached to any carbon on the ring and is selected from H, $C_1$-$C_6$ alkyl, halide, or perfluoroalkyl;

when X is C, $R^3$ is a fluoro and is attached to X;

$R^4$ and $R^5$ are each independently selected from H, $R^a$—O—$R^b$, $C_1$-$C_8$ alkyl, $C_2$-$C_8$ alkenyl, $C_2$-$C_8$ alkynyl, -$(R^d)_m$—$(C_3$-$C_{12}$ cycloalkyl), -$(R^d)_m$-aryl, -$(R^d)_m$-(3-15 membered heterocyclyl), -$(R^d)_m$—$(C_1$-$C_6$ perfluoroalkyl), -$(R^d)_m$halide, -$(R^d)_m$—CN, -$(R^d)_m$—C(O)$R^a$, -$(R^d)_m$—C(O)O$R^a$, -$(R^d)_m$—C(O)N$R^aR^b$, -$(R^d)_m$—O$R^a$, -$(R^d)_m$—OC(O)$R^a$, -$(R^d)_m$—OC(O)N$R^aR^b$, -$(R^d)_m$—O—S(O)$R^a$, -$(R^d)_m$—OS(O)$_2R^a$, -$(R^d)_m$—OS(O)$_2$N$R^aR^b$, -$(R^d)_m$—OS(O)N$R^aR^b$, -$(R^d)_m$—NO$_2$, -$(R^d)_m$—N$R^aR^b$, -$(R^d)_m$—N($R^a$)C(O)$R^b$, -$(R^d)_m$—N($R^a$)C(O)O$R^b$, -$(R^d)_m$—N($R^c$)C(O)N$R^aR^b$, -$(R^d)_m$—N($R^a$)S(O)$_2R^b$, -$(R^d)_m$—N($R^a$)S(O)$R^b$, -$(R^d)_m$—S$R^a$, -$(R^d)_m$—S(O)$R^a$, -$(R^d)_m$—S(O)$_2R^a$, -$(R^d)_m$—S(O)N$R^aR^b$, -$(R^d)_m$—S(O)$_2$N$R^aR^b$, —$(R^d)_m$—O—$(R^e)_m$—N$R^aR^b$ or $(R^d)_m$—N$R^a$-$(R^e)$—O$R^b$, or $R^4$ and $R^5$ may together cyclize to form a 3-to-5-membered spiro-cycloalkyl; wherein any of the said $C_3$-$C_{12}$ cycloalkyl, aryl, heterocyclyl, or heteroaryl are independently optionally further substituted by 0 to 3 $R_9$ groups;

$R^6$ is selected from $R^a$—O—$R^b$, $C_1$-$C_8$ alkyl, $C_2$-$C_8$ alkenyl, $C_2$-$C_8$ alkynyl, -$(R^d)_m$—$(C_3$-$C_{12}$ cycloalkyl), -$(R^d)_m$-aryl, -$(R^d)_m$-(3-15 membered heterocyclyl), -$(R^d)_m$—$(C_1$-$C_6$ perfluoroalkyl), -$(R^d)_m$-halide, -$(R^d)_m$—CN, -$(R^d)_m$—C(O)$R^a$, -$(R^d)_m$—C(O)O$R^a$, -$(R^d)_m$—C(O)N$R^aR^b$, -$(R^d)_m$—O$R^a$, -$(R^d)_m$—OC(O)$R^a$, -$(R^d)_m$—OC(O)N$R^aR^b$, -$(R^d)_m$—O—S(O)$R^a$, -$(R^d)_m$—OS(O)$_2R^a$, -$(R^d)_m$—OS(O)$_2$N$R^aR^b$, -$(R^d)_m$—

OS(O)NR$^a$R$^b$, -(R$^d$)$_m$—NO$_2$, -(R$^d$)$_m$—NR$^a$R$^b$, -(R$^d$)$_m$—N(R$^a$)C(O)R$^b$, -(R$^d$)$_m$—N(R$^a$)C(O)OR$^b$, -(R$^d$)$_m$—N(R$^c$)C(O)NR$^a$R$^b$, -(R$^d$)$_m$—N(R$^a$)S(O)$_2$R$^b$, -(R$^d$)$_m$—N(R$^a$)S(O)R$^b$, -(R$^d$)$_m$—SR$^a$, -(R$^d$)$_m$—S(O)R$^a$, —(R$^d$)$_m$—S(O)$_2$R$^a$, -(R$^d$)$_m$—S(O)NR$^a$R$^b$, -(R$^d$)$_m$—S(O)$_2$NR$^a$R$^b$, -(R$^d$)$_m$—O—(R$^e$)$_m$—NR$^a$R$^b$ or —(R$^d$)$_m$—NR$^a$—(R$^e$)—OR$^b$; or R$^6$ may together with R$^4$ cyclize to form a 4- to 7- membered heterocyclyl ring fused to the piperazine or piperadine to which they are attached; and wherein any of the said alkyl, alkenyl, alkynyl, cycloalkyl, aryl, heterocyclyl, and heteroaryl may independently be further substituted with 0 to 3 R$^9$ groups;

each R$^7$ and R$^8$ is independently C$_1$-C$_2$ alkyl, or R$^7$ and R$^8$ together cyclize to form a cyclopropyl or cyclobutyl;

each R$^9$ is independently selected from H, R$^a$—O—R$^b$, C$_1$-C$_8$ alkyl, C$_2$-C$_8$ alkenyl, C$_2$-C$_8$ alkynyl, -(R$^d$)$_m$—(C$_3$-C$_{12}$ cycloalkyl), -(R$^d$)$_m$-aryl, -(R$^d$)$_m$-(3-15 membered heterocyclyl), -(R$^d$)$_m$—(C$_1$- C$_6$ perfluoroalkyl), -(R$^d$)$_m$-halide, -(R$^d$)$_m$—CN, -(R$^d$)$_m$—C(O)R$^a$, -(R$^d$)$_m$—C(O)OR$^a$, -(R$^d$)$_m$—C(O)NR$^a$R$^b$, —(R$^d$)$_m$—OR$^a$, -(R$^d$)$_m$—OC(O)R$^a$, -(R$^d$)$_m$—OC(O)NR$^a$R$^b$, -(R$^d$)$_m$—O—S(O)R$^a$, -(R$^d$)$_m$—OS(O)$_2$R$^a$, -(R$^d$)$_m$—OS(O)$_2$NR$^a$R$^b$, -(R$^d$)$_m$—OS(O)NR$^a$R$^b$, -(R$^d$)$_m$—NO$_2$, -(R$^d$)$_m$—NR$^a$R$^b$, -(R$^d$)$_m$—N(R$^a$)C(O)R$^b$, -(R$^d$)$_m$—N(R$^a$)C(O)OR$^b$, -(R$^d$)$_m$—N(R$^e$)C(O)NR$^a$R$^b$, -(R$^d$)$_m$—N(R$^a$)S(O)$_2$R$^b$, -(R$^d$)$_m$—N(R$^a$)S(O)R$^b$, -(R$^d$)$_m$—SR$^a$, -(R$^d$)$_m$—S(O)R$^a$, -(R$^d$)$_m$—S(O)$_2$R$^a$, -(R$^d$)$_m$—S(O)NR$^a$R$^b$, -(R$^d$)$_m$—S(O)$_2$NR$^a$R$^b$, -(R$^d$)$_m$—O—(R$^d$)$_m$—NR$^a$R$^b$ or —(R$^d$)$_m$—NR$^a$-(R$^e$)—OR$^b$; and wherein any of the said alkyl, alkenyl, alkynyl, R$^d$, R$^e$, C$_3$-C$_{12}$ cycloalkyl, aryl or 3-15 membered heterocyclyl are independently optionally further substituted by 1-3 groups selected from —halide, C$_1$-C$_6$ alkyl, C$_1$-C$_6$ perfluoroalkyl, C$_1$-C$_6$alkoxyl, C$_1$-C$_6$alkylamino, CN or oxo;

each R$^a$, R$^b$ and R$^c$ is independently selected from H, C$_1$-C$_6$perfluoroalkyl, C$_1$-C$_8$ alkyl, C$_2$-C$_8$ alkenyl, —(C$_1$-C$_3$ alkylene)$_m$-(C$_3$-C$_8$ cycloalkyl), —(C$_1$-C$_3$ alkylene)$_m$-(C$_3$-C$_8$ cycloalkenyl), C$_2$-C$_8$ alkynyl, —(C$_1$-C$_3$ alkylene)$_m$-aryl, or —(C$_1$-C$_3$ alkylene)$_m$-(3-8 member heterocyclyl), and each R$^a$, R$^b$ and R$^c$ is independently optionally further substituted by 0 to 3 groups selected from halide, hydroxyl, —CN, C$_1$-C$_6$ alkyl, C$_1$-C$_6$ perfluoroalkyl, C$_1$-C$_6$ alkoxyl and C$_1$-C$_6$ alkylamino; or, when connected to the same nitrogen, R$^a$ and R$^b$ may optionally form a —(3-8 membered heterocyclyl), and said 3-8 membered heterocyclyl is optionally further substituted by 0 to 3 groups selected from halide, hydroxyl, —CN, C$_1$-C$_6$ alkyl, C$_1$-C$_6$ perfluoroalkyl, C$_1$-C$_6$ alkoxyl or C$_1$-C$_6$ alkylamino;

each R$^d$ and R$^e$ is independently —(C$_1$-C$_3$ alkylene)-, —(C$_2$-O$_5$ alkenylene)-, or —(C$_2$-C$_5$ alkynylene)-;

each m is independently 0 or 1; and with the proviso that if X=N, then R$^2$, R$^3$, R$^4$ and R$^5$ are not all H.

Another embodiment provides the method of treating a hematological malignancy, wherein R$^7$ and R$^8$ are both methyl. Another embodiment provides the method of treating a hematological malignancy, wherein X is N. Another embodiment provides the method of treating a hematological malignancy, wherein R$^1$ is a pyridine or a piperazine. Another embodiment provides the method of treating a hematological malignancy, wherein R$^1$ is a 5-membered heterocyclyl. Another embodiment provides the method of treating a hematological malignancy, wherein R$^1$ is selected from the group consisting of oxazole, isoxazole, thiazole or imidazole. Another embodiment provides the method of treating a hematological malignancy, wherein R$^2$ or R$^4$ is methyl. Another embodiment provides the method of treating a hematological malignancy, wherein R$^6$ is (R$^d$)$_m$-(3-15 membered heterocyclyl). Another embodiment provides the method of treating a hematological malignancy, wherein R$^6$ is (R$^d$)-tetrahydropyran. Another embodiment provides the method of treating a hematological malignancy, wherein R$^6$ is tetrahydro-2H-pyran-4-ylmethyl. Another embodiment provides the method of treating a hematological malignancy, wherein R$^2$ is CH$_3$ in (S) configuration. Another embodiment provides the method of treating a hematological malignancy, wherein R$^6$ is —(R$^d$)$_m$—OR$^a$.

One embodiment provides a method of treating a hematological malignancy in a subject in need thereof comprising administering to the subject a composition comprising a compound, or a pharmaceutically acceptable salt thereof, selected from the group consisting of:

N-(5-((2R,5S)-2,5-dimethyl-1-((tetrahydro-2H-pyran-4-yl)methyl)piperazine-4-carbonyl)-6,6-dimethyl-1,4,5,6-tetrahydropyrrolo[3,4-c]pyrazol-3-yl)picolinamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-fluoropyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-ethylisoxazole-3-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2,4-dimethyl-1,3-oxazole-5-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-methyl-1,3-thiazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-4-methyl-1,3-oxazole-5-carboxamide;

1-cyclobutyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1H-imidazole-4-carboxamide N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1-isopropyl-1H-imidazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-1,3-oxazole-4-carboxamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-morpholin-4-ylpyridine-2-carboxamide, and N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-(trifluoromethyppyridine-2-carboxamide.

One embodiment provides a method of treating a hematological malignancy in a subject in need thereof comprising administering to the subject a composition comprising a compound, or a pharmaceutically acceptable salt thereof, having formula (A):

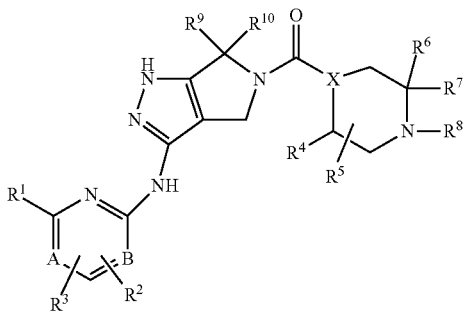

(A)

wherein
X is C—$R^{11}$ or N, wherein $R^{11}$ is H, halo, OH, $C_1$-$C_3$alkyl, $CF_3$, or CN;
A and B are independently C or N;
$R^1$, $R^2$ and $R^3$ are each independently selected from H, $R^a$—O—$R^b$, $C_1$-$C_8$ alkyl, $C_2$-$C_8$ alkenyl, $C_2$-$C_8$ alkynyl, -$(R^d)_m$—($C_3$-$C_{12}$ cycloalkyl), -$(R^d)_m$-phenyl, -$(R^d)_m$-(3-15 membered heterocycly), -$(R^d)_m$—($C_1$-$C_6$perfluoroalkyl), -$(R^d)_m$halide, -$(R^d)_m$—CN, -$(R^d)_m$—C(O)$R^a$, -$(R^d)_m$—C(O)O$R^a$, -$(R^d)_m$—C(O)NR$^a$R$^b$, -$(R^d)_m$—O$R^a$, -$(R^d)_m$—OC(O)$R^a$, -$(R^d)_m$—OC(O)NR$^a$R$^b$, -$(R^d)_m$—O—S(O)$R^a$, -$(R^d)_m$—OS(O)$_2$$R^a$, -$(R^d)_m$—OS(O)$_2$NR$^a$R$^b$, -$(R^d)_m$—OS(O)NR$^a$R$^b$, -$(R^d)_m$—NO$_2$, —$(R^d)_m$—NR$^a$R$^b$, -$(R^d)_m$—N($R^a$)C(O)$R^b$, -$(R^d)_m$—N($R^a$)C(O)O$R^b$, -$(R^d)_m$—N($R^c$)C(O)NR$^a$R$^b$, -$(R^d)_m$—N($R^a$)S(O)$_2$$R^b$, -$(R^d)_m$—N($R^a$)S(O)$R^b$, -$(R^d)_m$—S$R^a$, -$(R^d)_m$—S(O)$R^a$, -$(R^d)_m$—S(O)$_2$$R^a$, -$(R^d)_m$—S(O)NR$^a$R$^b$, -$(R^d)_m$—S(O)$_2$NR$^a$R$^b$, -$(R^d)_m$—O—$(R^e)_m$—NR$^a$R$^b$ or $(R^d)_m$—NR$^a$—$(R^e)$—O$R^b$; wherein $R^2$ and $R^3$ may together optionally cyclize to form a saturated or unsaturated 3-7 membered heterocyclyl fused to the 6-membered N-containing heteroaryl to which they are attached; and wherein any of the said alkyl, alkenyl, alkynyl, $R^a$, $R^b$, $R^c$, $R^d$, $R^e$, $C_3$-$C_{12}$ cycloalkyl, phenyl or 3-15 membered heterocyclyl, may independently be further optionally substituted by 0-3 $R^{12}$ groups;
$R^4$ and $R^5$ are each independently selected from H, $R^a$—O—$R^b$, $C_1$-$C_8$ alkyl, $C_2$-$C_8$ alkenyl, $C_2$-$C_8$ alkynyl, -$(R^d)_m$—($C_3$-$C_{12}$ cycloalkyl), -$(R^d)_m$-phenyl, -$(R^d)_m$-(3-15 membered heterocyclyl), -$(R^d)_m$—($C_1$-$C_6$ perfluoroalkyl), -$(R^d)_m$halide, -$(R^d)_m$—CN, -$(R^d)_m$—C(O)$R^a$, -$(R^d)_m$—C(O)O$R^a$, -$(R^d)_m$—C(O)NR$^a$R$^b$, -$(R^d)_m$—O$R^a$, -$(R^d)_m$—OC(O)$R^a$, $(R^d)_m$—OC(O)NR$^a$R$^b$, -$(R^d)_m$—O—S(O)$R^a$, -$(R^d)_m$—OS(O)$_2$$R^a$, -$(R^d)_m$—OS(O)$_2$NR$^a$R$^b$, -$(R^d)_m$—OS(O)NR$^a$R$^b$, -$(R^d)_m$—NO$_2$, $(R^d)_m$—NR$^a$R$^b$, $(R^d)_m$—N($R^a$)C(O)$R^b$, -$(R^d)_m$—N($R^a$)C(O)O$R^b$, -$(R^d)_m$—N($R^c$)C(O)NR$^a$R$^b$, -$(R^d)_m$—N($R^a$)S(O)$_2$$R^b$, -$(R^d)_m$—N($R^a$)S(O)$R^b$, -$(R^d)_m$—S$R^a$, -$(R^d)_m$—S(O)$R^a$, -(R)$_m$—S(O)$_2$$R^a$, -$(R^d)_m$—S(O)NR$^a$R$^b$, -$(R^d)_m$—S(O)$_2$NR$^a$R$^b$, -$(R^d)_m$—O—$(R^e)_m$—NR$^a$R$^b$ or —$(R^d)_m$—NR$^a$—$(R^e)$—O$R^b$; wherein any of the said alkyl, alkenyl, alkynyl, $R^a$, $R^b$, $R^c$, $R^d$, $R^e$, $C_3$-$C_{12}$ cycloalkyl, aryl or 3-15 membered heterocyclyl are independently optionally further substituted by 0-3 $R^{12}$ groups,
$R^6$ and $R^7$ are each independently H, $R^a$—O—$R^b$, $C_1$-$C_8$ alkyl, $C_2$-$C_8$ alkenyl, $C_2$-$C_8$ alkynyl, -$(R^d)_m$—($C_3$-$C_{12}$ cycloalkyl), -$(R^d)_m$-phenyl, -$(R^d)_m$-(3-15 membered heterocyclyl), -$(R^d)_m$—($C_1$-$C_6$ perfluoroalkyl), -$(R^d)_m$-halide, -$(R^d)_m$—CN, -$(R^d)_m$—C(O)$R^a$, -$(R^d)_m$—C(O)O$R^a$ —$(R^d)_m$—C(O)NR$^a$R$^b$, -$(R^d)_m$—O$R^a$, -$(R^d)_m$—OC(O)$R^a$, $(R^d)_m$—OC(O)NR$^a$R$^b$, -$(R^d)_m$—O—S(O)$R^a$, -$(R^d)_m$—OS(O)$_2$$R^a$, -$(R^d)_m$—OS(O)$_2$NR$^a$R$^b$, -$(R^d)_m$—OS(O)NR$^a$R$^b$, -$(R^d)_m$—NO$_2$, $(R^d)_m$—NR$^a$R$^b$, $(R^d)_m$—N($R^a$)C(O)$R^b$, -$(R^d)_m$—N($R^a$)C(O)O$R^b$, -$(R^d)_m$—N($R^c$)C(O)NR$^a$R$^b$, -$(R^d)_m$—N($R^a$)S(O)$_2$$R^b$, -$(R^d)_m$—N($R^a$)S(O)$R^b$, -$(R^d)_m$—S$R^a$, -$(R^d)_m$—S(O)$R^a$, -$(R^d)_m$—S(O)$_2$$R^a$, -$(R^d)_m$—S(O)NR$^a$R$^b$, -$(R^d)_m$—S(O)$_2$NR$^a$R$^b$, -$(R^d)_m$—O—$(R^e)_m$—NR$^a$R$^b$ or —$(R^d)_m$—NR$^a$-$(R^e)$—O$R^b$; wherein $R^6$ and $R^7$ may together optionally cyclize to form a $C_3$-$C_7$ cycloalkyl and wherein any of the said alkyl, alkenyl, alkynyl, $R^a$, $R^b$, $R^c$, $R^d$, $R^e$, $C_3$-$C_{12}$ cycloalkyl, aryl or 3-15 membered heterocyclyl are independently optionally further substituted by 0-3 $R^{12}$ groups;
$R^8$ is H, $R^a$—O—$R^b$, $C_1$-$C_8$ alkyl, $C_2$-$C_8$ alkenyl, $C_2$-$C_8$ alkynyl, -$(R^d)_m$—($C_3$-$C_{12}$ cycloalkyl), -$(R^d)_m$-phenyl, -$(R^d)_m$-(3-15 membered heterocyclyl), -$(R^d)_m$—($C_1$-$C_6$ perfluoroalkyl), -$(R^d)_m$halide, -$(R^d)_m$—CN, -$(R^d)_m$—C(O)$R^a$, -$(R^d)_m$—C(O)O$R^a$, -$(R^d)_m$—C(O)NR$^a$R$^b$, -$(R^d)_m$—O$R^a$, -$(R^d)_m$—OC(O)$R^a$, $(R^d)_m$—OC(O)NR$^a$R$^b$, -$(R^d)_m$—O—S(O)$R^a$, -$(R^d)_m$—OS(O)$_2$$R^a$, -$(R^d)_m$—OS(O)$_2$NR$^a$R$^b$, $(R^d)_m$—OS(O)NR$^a$R$^b$, -$(R^d)_m$—NO$_2$, $(R^d)_m$—NR$^a$R$^b$, $(R^d)_m$—N($R^a$)C(O)$R^b$, -$(R^d)_m$—N($R^a$)C(O)O$R^b$, -$(R^d)_m$—N($R^c$)C(O)NR$^a$R$^b$, -$(R^d)_m$—N($R^a$)S(O)$_2$$R^b$, -($(R^d)_m$—N($R^a$)S(O)$R^b$, -$(R^d)_m$—S$R^a$, -$(R^d)_m$—S(O)$R^a$, -$(R^d)_m$—S(O)$_2$$R^a$, -$(R^d)_m$—S(O)NR$^a$R$^b$, -$(R^d)_m$—S(O)$_2$NR$^a$R$^b$, -$(R^d)_m$—O—$(R^e)_m$—NR$^a$R$^b$ or $(R^d)_m$—NR$^a$-$(R^e)$—O$R^b$; and wherein any of the said alkyl, alkenyl, alkynyl, $R^a$, $R^b$, $R^c$, $R^d$, $R^e$, $C_3$-$C_{12}$ cycloalkyl, phenyl, or 3-15 membered heterocyclyl are independently optionally further substituted by 1-3 groups selected from F, $C_1$-$C_3$ alkyl, $C_1$-$C_3$ perfluoroalkyl, hydroxyl, $C_1$-$C_6$alkoxyl, or oxo;
$R^9$ and $R^{10}$ are each independently $C_1$-$C_2$ alkyl or can together cyclize to form a cyclopropyl or cyclobutyl;
each $R^{12}$ is independently H, $R^a$—O—$R^b$, $C_1$-$C_8$ alkyl, $C_2$-$C_8$ alkenyl, $C_2$-$C_8$ alkynyl, -$(R^d)_m$—($C_3$-$C_{12}$ cycloalkyl), -$(R^d)_m$-phenyl, -$(R^d)_m$-(3-15 membered heterocyclyl), -(Rd)$_m$-($C_1$-$C_6$ perfluoroalkyl), -$(R^d)_m$halide, -$(R^d)_m$—CN, -$(R^d)_m$—C(O)$R^d$, -$(R^d)_m$—C(O)O$R^a$, -$(R^d)_m$—C(O)NR$^a$R$^b$, -$(R^d)_m$—O$R^a$, -$(R^d)_m$—OC(O)$R^a$, $(R^d)_m$—OC(O)NR$^a$R$^b$, -$(R^d)_m$—O—S(O)$R^a$, -$(R^d)_m$—OS(O)$_2$$R^a$, -$(R^d)_m$—OS(O)$_2$NR$^a$R$^b$, -$(R^d)_m$—OS(O)NR$^a$R$^b$, -$(R^d)_m$—NO$_2$, $(R^d)_m$—NR$^a$R$^b$, -$(R^d)_m$—N($R^a$)C(O)$R^b$, -$(R^d)_m$—N($R^a$)C(O)O$R^b$, -$(R^d)_m$—N($R^c$)C(O)NR$^a$R$^b$, -$(R^d)_m$—N($R^a$)S(O)$_2$$R^b$, -$(R^d)_m$—N($R^a$)S(O)$R^b$, -$(R^d)_m$—S$R^a$, -$(R^d)_m$—S(O)$R^a$, -$(R^d)_m$—S(O)$_2$$R^a$, $(R^d)_m$—S(O)NR$^a$R$^b$, -$(R^d)_m$—S(O)$_2$NR$^a$R$^b$, -$(R^d)_m$—O—$(R^e)_m$—NR$^a$R$^b$ or —$(R^d)_m$—NR$^a$-$(R^e)$—O$R^b$; and wherein any of the said alkyl, alkenyl, alkynyl, $R^a$, $R^b$, $R^c$, $R^d$, $R^e$, $C_3$-$C_{12}$ cyclooalkyl, phenyl, or 3-15 membered heterocyclyl, are independently optionally further substituted by 1-3 groups selected from —F, $C_1$-$C_3$ alkyl, $C_1$-$C_3$ perfluoroalkyl, hydroxyl, $C_1$-$C_6$alkoxyl or oxo;
each $R^a$, $R^b$ and $R^c$ is independently selected from H, $C_1$-$C_8$ alkyl, $C_2$-$C_8$ alkenyl, -$(R^d)_m$—($C_3$-$C_8$ cycloalkyl), -$(R^d)_m$—($C_3$-$C_8$ cycloalkenyl), $C_2$-$C_8$ alkynyl, -$(R^d)_m$-phenyl, or —$(R^d)_m$-(3-7 membered heterocyclyl), and each $R^a$, $R^b$ and $R^c$ is independently optionally further substituted by 1-3 groups selected from halide, hydroxyl, —CN, $C_1$-$C_6$ alkyl, $C_1$-$C_6$ perfluoroalkyl, $C_1$-$C_6$ alkoxyl and $C_1$-$C_6$ alkylamino; or, when connected to the same nitrogen, $R^a$ and $R^b$ may together optionally form a 3-7 membered heterocyclyl, which may optionally be further substituted by 0-3 groups selected from halide, hydroxyl, —CN, $C_1$-$C_6$ alkyl, $C_1$-$C_6$ perfluoroalkyl, $C_1$-$C_6$ alkoxyl or $C_1$-$C_6$ alkylamino;

each $R^d$ and $R^e$ is independently -($C_1$-$C_3$ alkylene)-, —($C_2$-$C_5$ alkenylene)-, or —($C_2$-$C_5$ alkynylene)-; and each m is independently 0 or 1;

with the proviso that when X is N, $R^6$ and $R^7$ are not both H, and that when X is C—$R^{11}$, $R^6$ and $R^7$ are both H; or a pharmaceutically acceptable salt thereof.

Another embodiment provides a method of treating a hematological malignancy, wherein for the compound of Formula (A), $R^9$ and $R^{10}$ are both methyl. Another embodiment provides a method of treating a hematological malignancy, wherein for the compound of Formula (A), X is N and $R^6$ and $R^7$ are each independently H or $C_1$-$C_6$alkyl but are not both H. Another embodiment provides a method of treating a hematological malignancy, wherein for the compound of Formula (A), A is N and B is C. Another embodiment provides a method of treating a hematological malignancy, wherein for the compound of Formula (A), A is C and B is N. Another embodiment provides a method of treating a hematological malignancy, wherein for the compound of Formula (A), $R^6$ and $R^7$ are both methyl. Another embodiment provides a method of treating a hematological malignancy, wherein for the compound of Formula (A), $R^6$ is H and $R^7$ is methyl. Another embodiment provides a method of treating a hematological malignancy, wherein for the compound of Formula (A), $R^4$ is $R^a$—O—$R^b$, $C_1$-$C_8$ alkyl, $C_2$-$C_8$ alkenyl, $C_2$-$C_8$ alkynyl, -$(R^d)_m$—($C_3$-$C_{12}$cycloalkyl), -$(R^d)_m$-phenyl, -$(R^d)_m$-(3-15 membered heterocyclyl), -$(R^d)_m$—($C_1$-$C_6$perfluoroalkyl), -$(R^d)_m$-halide, -$(R_d)_m$—CN, -$(R_d)_m$—C(O)$R^a$, -$(R^d)_m$—C(O)O$R^a$, —$(R^d)_m$—C(O)NR$^a$R$^b$, -$(R^d)_m$—OR$^a$, -$(R^d)_m$—OC(O)$R^a$, $(R^d)_m$—OC(O)NR$^a$R$^b$, -$(R^d)_m$—O—S(O)$R^a$, -$(R^d)_m$OS(O)$_2$$R^a$, -$(R^d)_m$—OS(O)$_2$NR$^a$R$^b$, -$(R^d)_m$—OS(O)NR$^a$R$^b$, -$(R^d)_m$—NO$_2$, $(R^d)_m$—NR$^a$R$^b$, $(R^d)_m$N($R^a$)C(O)$R^b$, -$(R^d)_m$—N($R^a$)C(O)OR$^b$, -$(R^d)_m$—N($R^c$)C(O)NR$^a$R$^b$, -$(R^d)_m$—N($R^a$)S(O)$_2$$R^b$, -$(R^d)_m$N($R^a$)S(O)$R^b$, -$(R^d)_m$—SR$^a$, -$(R^d)_m$—S(O)$R^a$, -$(R^d)_m$—S(O)$_2$$R^a$, -$(R^d)_m$—S(O)NR$^a$R$^b$, —$(R^d)_m$-S(O)$_2$NR$^a$R$^b$, -$(R^d)_m$—O—$(R^e)_m$—NR$^a$R$^b$ or —$(R^d)_m$—NR$^a$—$(R^e)$—OR$^b$; wherein the said $R^a$, $R^b$, $R^c$, $R^d$, $R^e$, $C_3$-$C_{12}$ cycloalkyl, aryl, 3-15 membered heterocyclyl, are independently optionally further substituted by 0-3 $R^{12}$ groups. Another embodiment provides a method of treating a hematological malignancy, wherein for the compound of Formula (A), $R^4$ is methyl. Another embodiment provides a method of treating a hematological malignancy, wherein for the compound of Formula (A), $R^1$ is $R^a$—O—$R^b$, $C_1$-$C_8$ alkyl, $C_2$-$C_8$ alkenyl, $C_2$-$C_8$ alkynyl, -$(R^d)_m$—($C_3$-$C_{12}$ cycloalkyl), - $(R^d)_m$-phenyl, —$(R^d)_m$-(3-15 membered heterocyclyl), -$(R^d)_m$—($C_1$-$C_6$ perfluoroalkyl), -$(R^d)_m$-halide, -$(R^d)_m$—CN, -$(R^d)_m$—C(O)$R^a$, -$(R^d)_m$-C(O)O$R^a$, -$(R^d)_m$—C(O)NR$^a$R$^b$, -$(R^d)_m$—OR$^a$, -$(R^d)_m$—OC(O)$R^a$, $(R^d)_m$—OC(O)NR$^a$R$^b$, -$(R^d)_m$—O—S(O)$R^a$, -$(R^d)_m$—OS(O)$_2$$R^a$, -$(R^d)_m$—OS(O)$_2$NR$^a$R$^b$, -$(R^d)_m$—OS(O)NR$^a$R$^b$, -$(R^d)_m$—NO$_2$, -$(R^d)_m$NR$^a$R$^b$, $(R^d)_m$—N($R^a$)C(O)$R^b$, -$(R^d)_m$—N($R^a$)C(O)OR$^b$, -$(R^d)_m$—N($R^c$)C(O)NR$^a$R$^b$, —$(R^d)_m$—N($R^a$)S(O)$_2$$R^b$, -$(R^d)_m$—N($R^a$)S(O)$R^b$, -$(R^d)_m$—SR$^a$, -$(R^d)_m$—S(O)$R^a$, -$(R^d)_m$—S(O)$_2$$R^a$, -$(R^d)_m$—S(O)NR$^a$R$^b$, -$(R^d)_m$—S(O)$_2$NR$^a$R$^b$, -$(R^d)_m$—O—$(R^e)_m$—NR$^a$R$^b$ or —$(R^d)_m$—NR$^a$—$(R^e)$—OR$^b$; wherein the said- $R^a$, $R^b$, $R^c$, $R^d$, $R^e$, $C_3$-$C_{12}$ cycloalkyl, aryl, the said 3-15 membered heterocyclyl, are independently optionally further substituted by 0-3 $R^{12}$ groups.

Another embodiment provides a method of treating a hematological malignancy, wherein for the compound of Formula (A), $R^1$ is —$(R^d)_m$—OR$^a$, $C_1$-$C_8$ alkyl, or —$(R^d)_m$—NR$^a$R$^b$. Another embodiment provides a method of treating a hematological malignancy, wherein for the compound of Formula (A), $R^8$ is $R^a$—O—$R^b$, $C_1$-$C_8$ alkyl, $C_2$-$C_8$ alkenyl, $C_2$-$C_8$ alkynyl, -$(R^d)_m$—($C_3$-$C_{12}$ cycloalkyl), -$(R^d)_m$-phenyl, -$(R^d)_m$-(3-15 membered heterocyclyl), -$(R^d)_m$-($C_1$-$C_6$ perfluoroalkyl), -$(R^d)_m$-halide, -$(R^d)_m$—CN, -$(R^d)_m$—OR$^a$, or —$(R^d)_m$NR$^a$R$^b$. Another embodiment provides a method of treating a hematological malignancy, wherein for the compound of Formula (A), each $R^d$ and $R^e$ is independently an ($C_1$-$C_3$ alkylene).

One embodiment provides a method of treating a hematological malignancy in a subject in need thereof comprising administering to the subject a composition comprising a compound, or a pharmaceutically acceptable salt thereof, having formula (B):

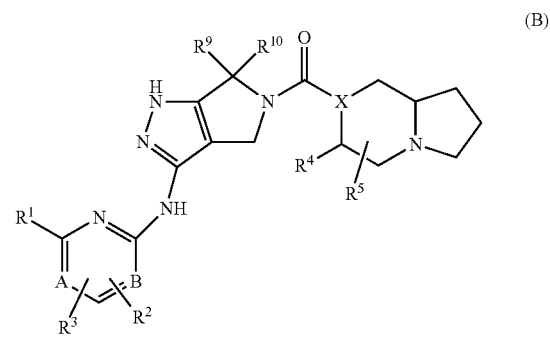

(B)

wherein

X is C—$R^{11}$ or N, wherein $R^{11}$ is H, halo, OH, $C_1$-$C_3$alkyl, CF$_3$, or CN;

A and B are independently C or N;

$R^1$ is $R^a$—O—$R^b$, $C_1$-$C_8$ alkyl, $C_2$-$C_8$ alkenyl, $C_2$-$C_8$ alkynyl, -$(R^d)_m$—($C_3$-$C_{12}$ cycloalkyl), -$(R^d)_m$—phenyl, -$(R^d)_m$-(3-15 membered heterocyclyl), -$(R^d)_m$-($C_1$-$C_6$perfluoroalkyl), -$(R^d)_m$-halide, -$(R^d)_m$—CN, —R$(^d)_m$—C(O)$R^a$, -$(R^d)_m$—C(O)O$R^a$, -$(R^d)_m$—C(O)NR$^a$R$^b$, -$(R^d)_m$—OR$^a$, -$(R^d)_m$—OC(O)$R^a$, ⁻$(R^d)_m$—OC(O)NR$^a$R$^b$, —$(R^d)_m$—O—S(O)$R^a$, -$(R^d)_m$—OS(O)$_2$$R^a$, -$(R^d)_m$—OS(O)$_2$NR$^a$R$^b$, -$(R^d)_m$—OS(O)NR$^a$R$^b$, —$(R^d)_m$—NO$_2$, $(R^d)_m$—NR$^a$R$^b$,$(R^d)_m$—N($R^a$)C(O)$R^b$, -$(R^d)_m$—N($R^a$)C(O)OR$^b$, -$(R^d)_m$—N($R^c$)C(O)NR$^a$R$^b$, —$(R^d)_m$—N($R^a$)S(O)$_2$$R^b$, -$(R^d)_m$—N($R^a$)S(O)$R^b$, -$(R^d)_m$—SR$^a$, -$(R^d)_m$—S(O)$R^a$, -$(R^d)_m$—S(O)$_2$$R^a$, -$(R^d)_m$—S(O)NR$^a$R$^b$, -$(R^d)_m$—S(O)$_2$NR$^a$R$^b$, -$(R^d)_m$13 O—$(R^e)_m$—NR$^a$R$^b$ or —$(R^d)_m$—NR$^a$—$(R^e)$—OR$^b$, and wherein any of the said alkyl, alkenyl, alkynyl, $R^a$, $R^b$, $R^c$, $R^d$, $R^e$, $C_3$-$C_{12}$ cycloalkyl, phenyl or 3-15 membered heterocyclyl, may independently be further optionally substituted by 0-3 $R^{12}$ groups;

$R^2$ and $R^3$ are each independently selected from H, $R^a$—O—$R^b$, $C_1$-$C_8$ alkyl, $C_2$-$C_8$ alkenyl, $C_2$-$C_8$ alkynyl, -$(R^d)_m$—($C_3$-$C_{12}$ cycloalkyl), -$(R^d)_m$-phenyl, -$(R^d)_m$-(3-15 membered heterocyclyl), -$(R^d)_m$—($C_1$-$C_6$perfluoroalkyl), -$(R^d)_m$-halide, -$(R^d)_m$—CN, —R$(^d)_m$—C(O)$R^a$, -$(R^d)_m$—C(O)O$R^a$-$(R)_m$—C(O)NR$^a$R$^b$,-$(R^d)_m$—OR$^a$, -$(R^d)_m$—OC(O)$R^a$, $(R^d)_m$—OC(O)NR$^a$R$^b$, -$(R^d)_m$—O—S(O)$R^a$, -$(R^d)_m$—OS(O)$_2$$R^a$, -$(R^d)_m$—OS(O)$_2$NR$^a$R$^b$, -$(R^d)_m$—OS(O)NR$^a$R$^b$, -$(R^d)_m$—NO$_2$,$(R^d)_m$—NR$^a$R$^b$, $(R^d)_m$—N($R^a$)C(O)$R^b$, -$(R^d)_m$—N($R^a$)C(O)OR$^b$, -$(R^d)_m$—N($R^c$)C(O)NR$^a$R$^b$, —$(R^d)_m$—N($R^a$)S(O)$_2$$R^b$, —$(R^d)_m$—N($R^a$)S(O)$R^b$, -$(R^d)_m$—SR$^a$, -$(R^d)_m$—S(O)$R^a$, -$(R^d)_m$—S(O)$_2$$R^a$, -$(R^d)_m$—S(O)NR$^a$R$^b$, -$(R^d)_m$—S(O)$_2$NR$^a$R$^b$, -$(R^d)_m$—O—$(R^e)_m$—NR$^a$R$^b$ or —$(R^d)_m$—NR$^a$-$(R^e)$—OR$^b$;

wherein $R^2$ and $R^3$ may together optionally cyclize to form a saturated or unsaturated 3-7 membered heterocyclyl fused to the 6-membered N-containing heteroaryl to which they are attached; and wherein any of the said alkyl, alkenyl, alkynyl, $R^a$, $R^b$, $R^c$, $R^d$, $R^e$, $C_3$-$C_{12}$ cycloalkyl, phenyl or 3-15 membered heterocyclyl, may independently be further optionally substituted by 0-3 $R^{12}$ groups;

$R^4$ and $R^5$ are each independently selected from H, $R^a$—O—$R^b$, $C_1$-$C_8$ alkyl, $C_2$-$C_8$ alkenyl, $C_2$-$C_8$ alkynyl, -$(R^d)_m$—$(C_3$-$C_{12}$ cycloalkyl), -$(R^d)_m$-phenyl, -$(R^d)_m$-(3-15 membered heterocyclyl), -$(R^d)_m$—$(C_1$-$C_6$ perfluoroalkyl), -$(R^d)_m$-halide, -$(R^d)_m$—CN, -$(R^d)_m$—C(O)$R^a$, -$(R^d)_m$—C(O)O$R^a$, -$(R^d)_m$—C(O)N$R^a R^b$, -$(R^d)_m$—O$R^a$, -$(R^d)_m$—OC(O)$R^a$, $(R^d)_m$—OC(O)N$R^a R^b$, -$(R^d)_m$—O—S(O)$R^a$, -$(R^d)_m$—OS(O)$_2 R^a$, -$(R^d)_m$—OS(O)$_2$N$R^a R^b$, -$(R^d)_m$—OS(O)N$R^a R^b$, -$(R^d)_m$—NO$_2$, $(R^d)_m$—N$R^a R^b$ $(R^d)_m$—N($R^a$)C(O)$R^b$, -$(R^d)_m$—N($R^a$)C(O)O$R^b$, -$(R^d)_m$—N($R^e$)C(O)N$R^a R^b$, -$(R^d)_m$—N($R^a$)S(O)$_2 R^b$, -$(R^d)_m$—N($R^a$)S(O)$R^b$, S$R^a$, -$(R^d)_m$—S(O)$R^a$, -$(R)_m$—S(O)$_2 R^a$, -$(R^d)_m$—S(O)N$R^a R^b$, -$(R^d)_m$—S(O)$_2$N$R^a R^b$, -$(R^d)_m$—O—$(R^e)_m$—N$R^a R^b$ or —$(R^d)_m$—N$R^a$—$(R^e)$—O$R^b$; wherein any of the said alkyl, alkenyl, alkynyl, $R^a$, $R^b$, $R^c$, $R^d$, $R^e$, $C_3$-$C_{12}$ cycloalkyl, aryl or 3-15 membered heterocyclyl are independently optionally further substituted by 0-3 $R^{12}$ groups, $R^8$ is H, $R^a$—O—$R^b$, $C_1$-$C_8$ alkyl, $C_2$-$C_8$ alkenyl, $C_2$-$C_8$ alkynyl, -$(R^d)_m$—$(C_3$-$C_{12}$ cycloalkyl), -$(R^d)_m$-phenyl, -$(R^d)_m$-(3-15 membered heterocyclyl), -$(R^d)_m$—$(C_1$-$C_6$ perfluoroalkyl), -$(R^d)_m$-halide, -$(R^d)_m$—CN, -$(R^d)_m$—C(O)$R^a$, -$(R^d)_m$—C(O)O$R^a$, -$(R^d)_m$—C(O)N$R^a R^b$, -$(R^d)_m$—O$R^a$, -$(R^d)_m$—OC(O)$R^a$, $(R^d)_m$—OC(O)N$R^a R^b$, -$(R^d)_m$—O—S(O)$R^a$, -$(R^d)_m$—OS(O)$_2 R^a$, -$(R^d)_m$—OS(O)$_2$N$R^a R^b$, -$(R^d)_m$—OS(O)N$R^a R^b$, -$(R^d)_m$—NO$_2$, -$(R^d)_m$—N$R^a R^b$, -$(R^d)_m$—N($R^a$)C(O)$R^b$, -$(R^d)_m$—N($R^a$)C(O)O$R^b$, -$(R^d)_m$—N($R^c$)C(O)N$R^a R^b$, -$(R^d)$, —N($R^a$)S(O)$_2 R^b$, - ($(R^d)_m$—N($R^a$)S(O)$R^b$, -$(R^d)_m$—S$R^a$, -$(R^d)_m$—S(O)$R^a$, -$(R^d)_m$—S(O)$_2 R^a$, -$(R^d)_m$—S(O)N$R^a R^b$, -$(R^d)_m$—S(O)$_2$N$R^a R^b$, -$(R^d)_m$—O—$(R^e)_m$—N$R^a R^b$ or $(R^d)_m$—N$R^a$-$(R^e)$—O$R^b$; and wherein any of the said alkyl, alkenyl, alkynyl, $R^a$, $R^b$, $R^c$, $R^d$, $R^e$, $C_3$-$C_{12}$ cycloalkyl, phenyl, or 3-15 membered heterocyclyl are independently optionally further substituted by 1-3 groups selected from —F, $C_1$-$C_3$ alkyl, $C_1$-$C_3$ perfluoroalkyl, hydroxyl, $C_1$-$C_6$alkoxyl, or oxo;

$R^9$ and $R^{10}$ are each independently $C_1$-$C_2$ alkyl or can together cyclize to form a cyclopropyl or cyclobutyl;

each $R^{12}$ is independently H, $R^a$—O—$R^b$, $C_1$-$C_8$ alkyl, $C_2$-$C_8$ alkenyl, $C_2$-$C_8$ alkynyl, -$(R^d)_m$—$(C_3$-$C_{12}$ cycloalkyl), -$(R^d)$, -phenyl, -$(R^d)_m$-(3-15 membered heterocyclyl), -$(R^d)_m$—$(C_1$-$C_6$ perfluoroalkyl), -$(R^d)_m$-halide, -$(R^d)_m$—CN, -$(R^d)_m$—C(O)$R^a$, -$(R^d)_m$—C(O)O$R^a$, -$(R^d)_m$—C(O)N$R^a R^b$, -$(R^d)_m$—O$R^a$, -$(R^d)_m$—OC(O)$R^a$, $(R^d)_m$—OC(O)N$R^a R^b$, -$(R^d)_m$—O—S(O)$R^a$, -$(R^d)_m$—OS(O)$_2 R^a$, -$(R^d)_m$—OS(O)$_2$N$R^a R^b$, -$(R^d)_m$—OS(O)N$R^a R^b$, -$(R^d)_m$—NO$_2$, $(R^d)_m$—N$R^a R^b$, $(R^d)_m$—N($R^a$)C(O)$R^b$, -$(R^d)_m$—N($R^a$)C(O)O$R^b$, -$(R^d)_m$—N($R^e$)C(O)N$R^a R^b$, -$(R^d)_m$—N($R^a$)S(O)$_2 R^b$, -$(R^d)_m$—N($R^a$)S(O)$R^b$, -$(R^d)_m$—S$R^a$, -$(R^d)_m$—S(O)$R^a$, -$(R^d)_m$—S(O)$_2 R^a$, -$(R^d)_m$—S(O)N$R^a R^b$, -$(R^d)_m$—S(O)$_2$N$R^a R^b$, -$(R^d)_m$—O$(R^e)_m$—N$R^a R^b$ or —$(R^d)_m$—N$R^a$-$(R^e)$—O$R^b$; and wherein any of the said alkyl, alkenyl, alkynyl, $R^a$, $R^b$, $R^c$, $R^d$, $R^e$, $C_3$-$C_{12}$ cycloalkyl, phenyl, or 3-15 membered heterocyclyl, are independently optionally further substituted by 1-3 groups selected from F, $C_1$-$C_3$ alkyl, $C_1$-$C_3$ perfluoroalkyl, hydroxyl, $C_1$-$C_6$alkoxyl or oxo;

each $R^a$, $R^b$ and $R^c$ is independently selected from H, $C_1$-$C_8$ alkyl, $C_2$-$C_8$ alkenyl, -$(R^d)_m$—$(C_3$-$C_8$ cycloalkyl), -$(R^d)_m$—$(C_3$-$C_8$ cycloalkenyl), $C_2$-$C_8$ alkynyl, -$(R^d)_m$-phenyl, or —$(R^d)_m$-(3-7 membered heterocyclyl), and each $R^a$, $R^b$ and $R^c$ is independently optionally further substituted by 1-3 groups selected from halide, hydroxyl, —CN, $C_1$-$C_6$ alkyl, $C_1$-$C_6$ perfluoroalkyl, $C_1$-$C_6$ alkoxyl and $C_1$-$C_6$ alkylamino; or, when connected to the same nitrogen, $R^a$ and $R^b$ may together optionally form a 3-7 membered heterocyclyl, which may optionally be further substituted by 0-3 groups selected from halide, hydroxyl, —CN, $C_1$-$C_6$ alkyl, $C_1$-$C_6$ perfluoroalkyl, $C_1$-$C_6$ alkoxyl or $C_1$-$C_6$ alkylamino;

each $R^d$ and $R^e$ is independently-($C_1$-$C_3$ alkylene)-, —($C_2$-$C_5$ alkenylene)-, or —($C_2$-$C_5$ alkynylene)-; and each m is independently 0 or 1, or a pharmaceutically acceptable salt thereof.

Another embodiment provides a method of treating a hematological malignancy, wherein for the compound of Formula (B), A is N and B is C. Another embodiment provides a method of treating a hematological malignancy, wherein for the compound of Formula (B), $R^9$ and $R^{10}$ are both methyl. Another embodiment provides a method of treating a hematological malignancy, wherein for the compound of Formula (B), $R^4$ is —$(R^d)_m$—O$R^d$, $C_1$-$C_8$ alkyl, $C_2$-$C_8$ alkenyl or $C_2$-$C_8$ alkynyl. Another embodiment provides a method of treating a hematological malignancy, wherein for the compound of Formula (B), $R^4$ is methyl. Another embodiment provides a method of treating a hematological malignancy, wherein for the compound of Formula (B), $R^1$ is —$(R^d)_m$—O$R^a$, $C_1$-$C_3$ alkyl, or —$(R^d)_m$—N$R^a R^b$. Another embodiment provides a method of treating a hematological malignancy, wherein for the compound of Formula (B), each $R^d$ and $R^e$ is independently an-($C_1$-$C_3$ alkylene)-.

One embodiment provides a method of treating a hematological malignancy in an individual in need thereof, comprising administering to the individual a pharmaceutical composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method wherein the hematological malignancy is a lymphoma or leukemia.

Another embodiment provides the method wherein the lymphoma or leukemia is a classical Hodgkin lymphoma, diffuse large B-cell lymphoma (DLBCL), follicular lymphoma, small lymphocytic lymphoma (SLL), chronic lymphocytic leukemia (CLL), mantle cell lymphoma, marginal zone B-cell lymphoma, Burkitt's lymphoma, lymphoplasmacytic lymphoma (Waldenstrom macroglobulinemia), hairy cell leukemia, primary central nervous system (CNS) lymphoma, acute lymphocytic leukemia (ALL), acute myeloid leukemia (AML), chronic myeloid leukemia (CML), or chronic myelomonocytic leukemia (CMML). Another embodiment provides the method wherein the diffuse large B-cell lymphoma (DLBCL) is activated B cell-like diffuse large B-cell lymphoma (ABC-DLBCL), germinal center B-celllike diffuse large B-cell lymphoma (GCB-DLBC), primary mediastinal B-cell lymphoma, or intravascular large B-cell lymphoma.

Another embodiment provides the method wherein the marginal zone B-cell lymphoma is extranodal marginal zone lymphoma, mucosa-associated lymphoid tissue (MALT) lymphoma, nodal marginal zone lymphoma, or splenic marginal zone lymphoma.

Another embodiment provides the method wherein the hematological malignancy is a relapsed or refractory hematological malignancy. Another embodiment provides the method wherein the relapsed or refractory hematological malignancy is a relapsed or refractory lymphoma or leukemia. Another embodiment provides the method wherein the relapsed or refractory lymphoma or leukemia is relapsed or refractory classical Hodgkin lymphoma, relapsed or refractory diffuse large B-cell lymphoma (DLBCL), relapsed or refractory follicular lymphoma, relapsed or refractory small lymphocytic lymphoma (SLL), relapsed or refractory chronic lymphocytic leukemia (CLL), relapsed or refractory mantle cell lymphoma, relapsed or refractory marginal zone B-cell lymphoma, relapsed or refractory Burkitt's lymphoma, relapsed or refractory lymphoplasmacytic lymphoma (Waldenstrom macroglobulinemia), relapsed or refractory hairy cell leukemia, relapsed or refractory primary central nervous system (CNS) lymphoma, relapsed or refractory acute lymphocytic leukemia (ALL), relapsed or refractory acute myeloid leukemia (AML), relapsed or refractory chronic myeloid leukemia (CML), or relapsed or refractory chronic myelomonocytic leukemia (CMML).

One embodiment provides a method of treating a hematological malignancy in an individual in need thereof, comprising administering to the individual a pharmaceutical composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, wherein the use of ibritinub is unsuitable or otherwise contraindicated.

One embodiment provides a method of treating a diffuse large B-cell lymphoma (DLBCL) in an individual in need thereof, comprising administering to the individual a pharmaceutical composition comprising 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method wherein the DLBCL is ABC- DLBCL.

One embodiment provides a method of treating a relapsed or refractory diffuse large B-cell lymphoma (DLBCL) in an individual in need thereof, comprising administering to the individual a pharmaceutical composition comprising 5-{[(2S,5R)-2,5-dimethyl-4-(tetrahydro-2H-pyran-4-ylmethyl)piperazin-1-yl]carbonyl}-N-(5-fluoro-2-methyl pyrimidin-4-yl)-6,6-dimethyl-1,4,5,6-tetrahydropyrrolo[3,4-c]pyrazol-3-amine, or a pharmaceutically acceptable salt thereof. Another embodiment provides the method wherein the relapsed or refractory diffuse large B-cell lymphoma (DLBCL) is refractory to a BTK inhibitor. Another embodiment provides the method wherein the BTK inhibitor is ibrutinib. Another embodiment provides the method wherein the DLBCL is ABC-DLBCL.

One embodiment provides a method of treating a chronic lymphocytic leukemia (CLL) in an individual in need thereof, comprising administering to the individual a pharmaceutical composition comprising 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method further comprising administration of selinexor.

One embodiment provides a method of treating a relapsed or refractory chronic lymphocytic leukemia (CLL) in an individual in need thereof, comprising administering to the individual a pharmaceutical composition comprising 5-{[(2S,5R)-2,5-Dimethyl-4-(tetrahydro-2H-pyran-4-ylmethyl)piperazin-1-yl]carbonyl}-N-(5-fluoro-2-methyl pyrimidin-4-yl)-6,6-dimethyl-1,4,5,6-tetrahydropyrrolo[3, 4-c]pyrazol-3-amine, or a pharmaceutically acceptable salt thereof. Another embodiment provides the method wherein the relapsed or refractory chronic lymphocytic leukemia (CLL) is refractory to a BTK inhibitor. Another embodiment provides the method wherein the BTK inhibitor is ibrutinib. Another embodiment provides the method further comprising administration of selinexor.

One embodiment provides a method of treating a chronic lymphocytic leukemia (CLL) in an individual in need thereof, comprising administering to the individual: (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; (b) a BTK inhibitor; and (c) a composition comprising selinexor. Another embodiment provides the method wherein the BTK inhibitor is ibrutinib.

One embodiment provides a method of treating a relapsed or refractory chronic lymphocytic leukemia (CLL) in an individual in need thereof, comprising administering to the individual: (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; and (b) a composition comprising selinexor. Another embodiment provides the method wherein the relapsed or refractory chronic lymphocytic leukemia (CLL) is refractory to a BTK inhibitor. Another embodiment provides the method wherein the BTK inhibitor is ibrutinib.

One embodiment provides a method of treating a diffuse large B-cell lymphoma (DLBCL) in an individual in need thereof, comprising administering to the individual: (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; and (b) a BTK inhibitor. Another embodiment provides the method wherein the BTK inhibitor is ibrutinib. Another embodiment provides the method wherein the DLBCL is ABC- DLBCL.

One embodiment provides a method of treating a chronic lymphocytic leukemia (CLL) in an individual in need thereof, comprising administering to the individual: (a) a composition comprising 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; and (b) a BTK inhibitor. Another embodiment provides the method wherein the BTK inhibitor is ibrutinib.

One embodiment provides a method of treating an acute myeloid leukemia (AML) in an individual in need thereof, comprising administering to the individual a pharmaceutical composition comprising 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof.

One embodiment provides a method of treating a relapsed or refractory acute myeloid leukemia (AML) in an individual in need thereof, comprising administering to the individual a pharmaceutical composition comprising 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof.

One embodiment provides a method of treating a acute myeloid leukemia (AML) in an individual in need thereof, comprising administering to the individual: (a) a composition comprising 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; and (b) a BTK inhibitor. Another embodiment provides the method wherein the BTK inhibitor is ibrutinib.

One embodiment provides a method of treating multiple myeloma in an individual in need thereof, comprising administering to the individual a pharmaceutical composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method wherein the multiple myeloma is relapsed or refractory multiple myeloma. Another embodiment provides the method wherein the relapsed or refractory multiple myeloma is refractory to a BTK inhibitor. Another embodiment provides the method wherein the BTK inhibitor is ibrutinib.

One embodiment provides a method of treating a multiple myeloma in an individual in need thereof, comprising administering to the individual: (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; and (b) a BTK inhibitor. Another embodiment provides the method wherein the BTK inhibitor is ibrutinib.

One embodiment provides a method of treating a Ewing's sarcoma in an individual in need thereof, comprising administering to the individual a pharmaceutical composition comprising 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof.

One embodiment provides a method of treating a small lymphocytic lymphoma (SLL) in an individual in need thereof, comprising administering to the individual a pharmaceutical composition comprising 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method further comprising administration of selinexor.

One embodiment provides a method of treating a relapsed or refractory small lymphocytic lymphoma (SLL) in an individual in need thereof, comprising administering to the individual a pharmaceutical composition comprising 5-{[(2S,5R)-2,5-Dimethyl-4-(tetrahydro-2H-pyran-4-ylmethyl)piperazin-1-yl]carbonyl}-N-(5-fluoro-2-methyl pyrimidin-4-yl)-6,6-dimethyl-1,4,5,6-tetrahydropyrrolo[3,4-c]pyrazol-3-amine, or a pharmaceutically acceptable salt thereof. Another embodiment provides the method wherein the relapsed or refractory small lymphocytic lymphoma (SLL) is refractory to a BTK inhibitor. Another embodiment provides the method wherein the BTK inhibitor is ibrutinib.

Another embodiment provides the method further comprising administration of selinexor.

One embodiment provides a method of treating a small lymphocytic lymphoma (SLL) in an individual in need thereof, comprising administering to the individual: (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; (b) a BTK inhibitor; and (c) a composition comprising selinexor. Another embodiment provides the method wherein the BTK inhibitor is ibrutinib.

One embodiment provides a method of treating a relapsed or refractory small lymphocytic lymphoma (SLL) in an individual in need thereof, comprising administering to the individual: (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; and (b) a composition comprising selinexor. Another embodiment provides the method wherein the relapsed or refractory small lymphocytic lymphoma (SLL) is refractory to a BTK inhibitor. Another embodiment provides the method wherein the BTK inhibitor is ibrutinib.

One embodiment provides a method of treating a B-cell derived hematologic malignancy in an individual in need thereof, comprising administering to the individual a pharmaceutical composition comprising 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. In some instances, the B-cell derived hematologic malignancy comprises a classical Hodgkin lymphoma, diffuse large B-cell lymphoma (DLBCL), follicular lymphoma, small lymphocytic lymphoma (SLL), chronic lymphocytic leukemia (CLL), mantle cell lymphoma, multiple myeloma, marginal zone B-cell lymphoma, Burkitt's lymphoma, lymphoplasmacytic lymphoma (Waldenstrom macroglobulinemia), hairy cell leukemia, primary central nervous system (CNS) lymphoma, acute lymphocytic leukemia (ALL), acute myeloid leukemia (AML), chronic myeloid leukemia (CML), or chronic myelomonocytic leukemia (CMML). In some instances, the B-cell derived hematologic malignancy comprises DLBCL. In some instances, the B-cell derived hematologic malignancy comprises CLL. In some instances, the B-cell derived hematologic malignancy comprises SLL. In some instances, the B-cell derived hematologic malignancy comprises multiple myeloma. In some instances, the B-cell derived hematologic malignancy comprises AML. In some instances, the method further comprises administration of selinexor to the individual. In additional instances, the method further comprises administration of a BTK inhibitor. In some cases, the BTK inhibitor is ibrutinib.

One embodiment provides a method of treating a B-cell derived hematologic malignancy in an individual in need thereof, comprising administering to the individual: (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; (b) a BTK inhibitor; and (c) a composition comprising selinexor. In some instances, the B-cell derived hematologic malignancy comprises a classical Hodgkin lymphoma, diffuse large B-cell lymphoma (DLBCL), follicular lymphoma, small lymphocytic lymphoma (SLL), chronic lymphocytic leukemia (CLL), mantle cell lymphoma, marginal zone B-cell lymphoma, Burkitt's lymphoma, lymphoplasmacytic lymphoma (Waldenstrom macroglobulinemia), hairy cell leukemia, primary central nervous system (CNS) lymphoma, multiple myeloma, acute lymphocytic leukemia (ALL), acute myeloid leukemia (AML), chronic myeloid leukemia (CML), or chronic myelomonocytic leukemia (CMML). In some instances, the B-cell derived hematologic malignancy comprises DLBCL. In some instances, the B-cell derived hematologic malignancy comprises CLL. In some instances, the B-cell derived hematologic malignancy comprises SLL. In some instances, the B-cell derived hematologic malignancy comprises multiple myeloma. In some instances, the B-cell derived hematologic malignancy comprises AML. In some cases, the BTK inhibitor is ibrutinib.

One embodiment provides a method of treating a refractory B-cell derived hematologic malignancy in an individual in need thereof, comprising administering to the individual a pharmaceutical composition comprising 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. In some instances, the refractory B-cell derived hematologic malignancy comprises a classical Hodgkin lymphoma, refractory diffuse large B-cell lymphoma (DLBCL), refractory follicular lymphoma, refractory small lymphocytic lymphoma (SLL), refractory chronic lymphocytic leukemia (CLL), refractory mantle cell lymphoma, refractory marginal zone B-cell lymphoma, refractory Burkitt's lymphoma, refractory lymphoplasmacytic lymphoma (Waldenstrom macroglobulinemia), refractory hairy cell leukemia, refractory primary central nervous system (CNS) lymphoma, refractory multiple myeloma, refractory acute lymphocytic leukemia (ALL), refractory acute myeloid leukemia (AML), refractory chronic myeloid leukemia (CML), or refractory chronic myelomonocytic leukemia (CMML). In some instances, the refractory B-cell derived hematologic malignancy comprises refractory DLBCL. In some instances, the refractory B-cell derived hematologic malignancy comprises refractory CLL. In some instances, the refractory B-cell derived hematologic malignancy comprises refractory SLL. In some instances, the refractory B-cell derived hematologic malignancy comprises refractory multiple myeloma. In some instances, the refractory B-cell derived hematologic malignancy comprises refractory AML. In some instances, the method further comprises administration of selinexor to the individual. In additional instances, the method further comprises administration of a BTK inhibitor. In some cases, the BTK inhibitor is ibrutinib.

In some instances, the relapsed or refractory B-cell derived hematologic malignancy expresses a mutation in BTK protein, or PLCγ2, or both. One embodiment provides a method of treating an individual having a BTK and/or PLCγ2 mutation, comprising administering to the individual a pharmaceutical composition comprising 5-{[(2S,5R)-2,5-Dimethyl-4-(tetrahydro-2H-pyran-4-ylmethyl)piperazin-1-yl]carbonyl}-N-(5-fluoro-2-methyl pyrimidin-4-yl)-6,6-dimethyl-1,4,5,6-tetrahydropyrrolo[3,4-c]pyrazol-3-amine, or a pharmaceutically acceptable salt thereof, wherein the presence of a mutation in BTK and/or PLCγ2 leads to a resistance to a BTK inhibitor. In some instances, the BTK mutation comprises a mutation at residue C481. In some cases, the mtuation is C481S In some instances, the PLCγ2 mutation comprises a mutation at residue R665 and/or L845.

In some cases, the mutation is R665W. In some cases, the mutation is L845F. In some instances, the individual has a B-cell derived hematologic malignancy. In some instances, the individual has a classical Hodgkin lymphoma, diffuse large B-cell lymphoma (DLBCL), follicular lymphoma, small lymphocytic lymphoma (SLL), chronic lymphocytic leukemia (CLL), mantle cell lymphoma, multiple myeloma, marginal zone B-cell lymphoma, Burkitt's lymphoma, lymphoplasmacytic lymphoma (Waldenstrom macroglobulinemia), hairy cell leukemia, primary central nervous system (CNS) lymphoma, acute lymphocytic leukemia (ALL), acute myeloid leukemia (AML), chronic myeloid leukemia (CML), or chronic myelomonocytic leukemia (CIVIML). In some instances, the individual has DLBCL. In some instances, the individual has CLL. In some instances, the individual has SLL. In some instances, the individual has multiple myeloma. In some instances, the individual has AML. In some instances, the method further comprises administration of selinexor to the individual. In additional instances, the method further comprises administration of ibrutinib.

One embodiment provides a method of treating an individual having a BTK and/or PLCγ2 mutation, comprising administering to the individual: (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; (b) ibrutinib; and (c) a composition comprising selinexor; wherein the presence of a mutation in BTK and/or PLCγ2 leads to a resistance to a BTK inhibitor. In some instances, the BTK mutation comprises a mutation at residue C481. In some cases, the mtuation is C481S. In some instances, the PLCγ2 mutation comprises a mutation at residue R665 and/or L845. In some cases, the mutation is R665W. In some cases, the mutation is L845F. In some instances, the individual has a B-cell derived hematologic malignancy. In some instances, the individual has a classical Hodgkin lymphoma, diffuse large B-cell lymphoma (DLBCL), follicular lymphoma, small lymphocytic lymphoma (SLL), chronic lymphocytic leukemia (CLL), mantle cell lymphoma, multiple myeloma, marginal zone B-cell lymphoma, Burkitt's lymphoma, lymphoplasmacytic lymphoma (Waldenstrom macroglobulinemia), hairy cell leukemia, primary central nervous system (CNS) lymphoma, acute lymphocytic leukemia (ALL), acute myeloid leukemia (AML), chronic myeloid leukemia (CML), or chronic myelomonocytic leukemia (CMML). In some instances, the individual has DLBCL. In some instances, the individual has CLL. In some instances, the individual has SLL. In some instances, the individual has multiple myeloma. In some instances, the individual has AML.

One embodiment provides a method of treating a refractory B-cell derived hematologic malignancy in an individual in need thereof, comprising administering to the individual: (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; (b) a BTK inhibitor; and (c) a composition comprising selinexor. In some instances, the refractory B-cell derived hematologic malignancy comprises a classical Hodgkin lymphoma, refractory diffuse large B-cell lymphoma (DLBCL), refractory follicular lymphoma, refractory small lymphocytic lymphoma (SLL), refractory chronic lymphocytic leukemia (CLL), refractory mantle cell lymphoma, refractory marginal zone B-cell lymphoma, refractory Burkitt's lymphoma, refractory lymphoplasmacytic lymphoma (Waldenstrom macroglobulinemia), refractory hairy cell leukemia, refractory multiple myeloma, refractory primary central nervous system (CNS) lymphoma, refractory acute lymphocytic leukemia (ALL), refractory acute myeloid leukemia (AML), refractory chronic myeloid leukemia (CML), or refractory chronic myelomonocytic leukemia (CMML). In some instances, the refractory B-cell derived hematologic malignancy comprises refractory DLBCL. In some instances, the refractory B-cell derived hematologic malignancy comprises refractory CLL. In some instances, the refractory B-cell derived hematologic malignancy comprises refractory SLL. In some instances, the refractory B-cell derived hematologic malignancy comprises refractory multiple myeloma. In some instances, the refractory B-cell derived hematologic malignancy comprises refractory AML. In some cases, the BTK inhibitor is ibrutinib.

One embodiment provides a method of treating an ibrutinib-resistant individual, comprising administering to the individual a pharmaceutical composition comprising 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. In some instances, the ibrutinib-resistant individual has a B-cell derived hematologic malignancy. In some instances, the ibrutinib-resistant individual has a classical Hodgkin lymphoma, diffuse large B-cell lymphoma (DLBCL), follicular lymphoma, small lymphocytic lymphoma (SLL), chronic lymphocytic leukemia (CLL), mantle cell lymphoma, multiple myeloma, marginal zone B-cell lymphoma, Burkitt's lymphoma, lymphoplasmacytic lymphoma (Waldenstrom macroglobulinemia), hairy cell leukemia, primary central nervous system (CNS) lymphoma, acute lymphocytic leukemia (ALL), acute myeloid leukemia (AML), chronic myeloid leukemia (CML), or chronic myelomonocytic leukemia (CMML). In some instances, the ibrutinib-resistant individual has DLBCL. In some instances, the ibrutinib-resistant individual has CLL. In some instances, the ibrutinib-resistant individual has SLL. In some instances, the ibrutinib-resistant individual has multiple myeloma. In some instances, the ibrutinib-resistant individual has AML. In some instances, the method further comprises administration of selinexor to the individual. In additional instances, the method further comprises administration of ibrutinib.

One embodiment provides a method of treating an ibrutinib-resistant individual, comprising administering to the individual: (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; (b) ibrutinib; and (c) a composition comprising selinexor. In some instances, the ibrutinib-resistant individual has a B-cell derived hematologic malignancy. In some instances, the ibrutinib-resistant individual has a classical Hodgkin lymphoma, diffuse large B-cell lymphoma (DLBCL), follicular lymphoma, small lymphocytic lymphoma (SLL), chronic lymphocytic leukemia (CLL), mantle cell lymphoma, marginal zone B-cell lymphoma, multiple myeloma, Burkitt's lymphoma, lymphoplasmacytic lymphoma (Waldenstrom macroglobulinemia), hairy cell leukemia, primary central nervous system (CNS) lymphoma, acute lymphocytic leukemia (ALL), acute myeloid leukemia (AML), chronic myeloid leukemia (CML), or chronic myelomonocytic leukemia (CMML). In some instances, the ibrutinib-resistant individual has DLBCL. In some instances, the ibrutinib-resistant individual has CLL. In some instances, the ibrutinib-resistant individual has SLL. In some instances, the ibrutinib-resistant individual has multiple myeloma. In some instances, the ibrutinib-resistant individual has AML.

One embodiment provides a method of inducing lymphocytosis in a first individual, comprising administering to the first individual a pharmaceutical composition comprising 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, wherein the lymphocyte count is increased in the first individual relative to a second individual without the administration of the pharmaceutical composition. k some instances, the lymphocyte count is increased by at least 10%, 15%, 20%, 25%, 30%, 40%, 50%, 60%, 70%, 80%, 90%, or 99%, relative to a second individual without the administration of the pharmaceutical composition. In some instances, the lymphocyte count is higher than 3000 lymphocytes per microliter of blood in the first individual after administration of the pharmaceutical composition.

One embodiment provides a method of inducing lymphocytosis in a first individual, comprising administering to the first individual: (a) a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; (b) ibrutinib; and (c) a composition comprising selinexor; wherein the lymphocyte count is increased in the first individual relative to a second individual without the administration of the compositions of (a), (b), and (c). In some instances, the lymphocyte count is increased by at least 10%, 15%, 20%, 25%, 30%, 40%, 50%, 60%, 70%, 80%, 90%, or 99%, relative to the second individual. In some instances, the lymphocyte count is higher than 3000 lymphocytes per microliter of blood in the first individual post-administration.

One embodiment provides a method for inducing apoptosis in a cell comprising administering to the cell an effective amount of a composition comprising 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof.

One embodiment provides a method for decreasing cell proliferation in a cell comprising administering to the cell an effective amount of a composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof.

Combination Therapy

In some instances, the methods described herein further comprise combination therapy with at least one additional oncology therapeutic agent. One embodiment provides a method of treating a hematological malignancy in an individual in need thereof, comprising administering to the individual: (a) a composition comprising a compound of formula (I), formula (A) or formula (B), or a pharmaceutically acceptable salt thereof; and (b) at least one oncology therapeutic selected from a SYK inhibitor, a dual SYK-JAK inhibitor, a PI3K inhibitor, a JAK-STAT inhibitor, a BCL2 inhibitor, an immunomodulatory agent, an antibody-drug coojugate, an immune checkpoint inhibitor, a PD-1 inhibitor, a TIM-3 inhibitor, a CTLA-4 inhibitor, a bromodomain inhibitor, an EZH2 inhibitor, an HDAC inhibitor, or an IDH2 inhibitor.

One embodiment provides a method of treating a hematological malignancy in an individual in need thereof, comprising administering to the individual: (a) a composition comprising 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof; and (b) at least one oncology therapeutic selected from a SYK inhibitor, a dual SYK-JAK inhibitor, a PI3K inhibitor, a JAK-STAT inhibitor, a BCL2 inhibitor, an immunomodulatory agent, an antibody-drug coojugate, an immune checkpoint inhibitor, a PD-1 inhibitor, a TIM-3 inhibitor, a CTLA-4 inhibitor, a bromodomain inhibitor, an EZH2 inhibitor, an HDAC inhibitor, or an IDH2 inhibitor.

Another embodiment provides the method wherein the hematological malignancy is a lymphoma or leukemia. Another embodiment provides the method wherein the lymphoma or leukemia is a classical Hodgkin lymphoma, diffuse large B-cell lymphoma (DLBCL), follicular lymphoma, small lymphocytic lymphoma (SLL), chronic lymphocytic leukemia (CLL), mantle cell lymphoma, marginal zone B-cell lymphoma, Burkitt's lymphoma, lymphoplasmacytic lymphoma (Waldenstrom macroglobulinemia), hairy cell leukemia, primary central nervous system (CNS) lymphoma, acute lymphocytic leukemia (ALL), acute myeloid leukemia (AML), chronic myeloid leukemia (CML), or chronic myelomonocytic leukemia (CMML). Another embodiment provides the method wherein the hematological malignancy is a relapsed or refractory hematological malignancy. Another embodiment provides the method wherein the relapsed or refractory hematological malignancy is a relapsed or refractory lymphoma or leukemia.

Pharmaceutical Compositions and Dosage Forms

The pyrrolo-pyrazole compounds used in the methods described herein are, in some instances, administered orally as tablets or capsules, as oily or aqueous suspensions, lozenges, troches, powders, granules, emulsions, syrups or elixirs. The compositions for oral use may include one or more agents for flavoring, sweetening, coloring and preserving in order to produce pharmaceutically elegant and palatable preparations. Tablets may contain pharmaceutically acceptable excipients as an aid in the manufacture of such tablets. As is conventional in the art these tablets may be coated with a pharmaceutically acceptable enteric coating, such as glyceryl monostearate or glyceryl distearate, to delay disintegration and absorption in the gastrointestinal tract to provide a sustained action over a longer period.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain active ingredients in admixture with excipients suitable for the manufacture of an aqueous suspension. Such excipients may be a suspending agent, such as sodium carboxymethyl cellulose, methyl cellulose, hydroxypropylmethyl cellulose, sodium alginate, polyvinylpyrrolidone, gum tragacanth and gum acacia; a dispersing or wetting agent that may be a naturally occurring phosphatide such as lecithin, a condensation product of ethylene oxide and a long chain fatty acid, for example polyoxyethylene stearate, a condensation product of ethylene oxide and a long chain aliphatic alcohol such as heptadecaethylenoxycetanol, a condensation product of ethylene oxide and a partial ester derived from a fatty acid and hexitol such as polyoxyethylene sorbitol monooleate or a fatty acid hexitol anhydrides such as polyoxyethylene sorbitan monooleate.

The pyrrolo-pyrazole compounds used in the methods described herein are, in some instances, in the form of a sterile injectable aqueous or oleagenous suspension. This suspension may be formulated according to know methods using those suitable dispersing or wetting agents and suspending agents that have been mentioned above. The sterile injectable preparation may also be formulated as a suspension in a non toxic perenterally-acceptable diluent or solvent, for example as a solution in 1,3-butanediol. Among the acceptable vehicles and solvents that may be employed are water, Ringers solution and isotonic sodium chloride solution. For this purpose any bland fixed oil may be employed including synthetic mono- or diglycerides. In addition fatty acids such as oleic acid find use in the preparation of injectables.

Dosage levels of the pyrrolo-pyrazole compounds to be used for the methods of treatment disclosed herein range from about 0.5 mg/kg body weight to about 100 mg/kg body weight. A preferred dosage range is between about 30 mg/kg body weight to about 100 mg/kg body weight.

In some embodiments, the pyrrolo-pyrazole compounds described herein have a half-life of from 10 hours to 20 hours. In some instances, the pyrrolo-pyrazole compounds described herein have a half-life of from 12 hours to 20 hours, 12 hours to 18 hours, or 12 hours to 15 hours. In some cases, the pyrrolo-pyrazole compounds described herein have a half-life of about 10 hours, 11 hours, 12 hours, 13 hours, 14 hours, 15 hours, 16 hours, 17 hours, 18 hours, 19 hours, or 20 hours.

EXAMPLES

These examples are provided for illustrative purposes only and not to limit the scope of the claims provided herein.

Compound A refers to 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, which was disclosed in WO 2008/096260 and having the chemical structure:

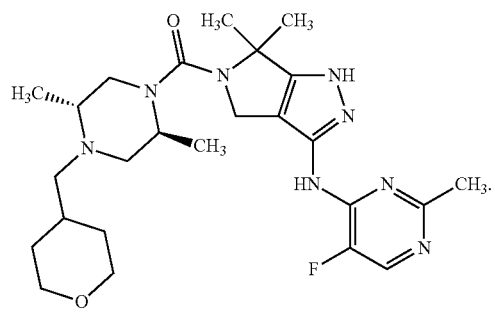 [SMILES: Cc1ncc(F)c(Nc2n[nH]c3c2CN(C(=O)N2C[C@@H](C)N(CC4CCOCC4)C[C@@H]2C)C3(C)C)n1]

Example 1: Compound A is an Isoform Selective PKC Inhibitor

A summary of PKC inhibition by compound A is provided in Table 1. The methods for these determinations have been described (Grant, et al. 2010, Eur J Pharmacol. 627:16-25). Compound A is a potent, ATP-competitive and reversible inhibitor of conventional PKC enzymes with a Ki=5.3 nM for recombinant PKC beta and a Ki=10.4 nM for recombinant PKC alpha. Compound A is also is a potent inhibitor of the novel isoform PKC theta with an $IC_{50}$=25.6 nM. While Compound A demonstrated some potency for conventional isoform PKC gamma with an $IC_{50}$=57.5 nM, Compound A demonstrated a high degree of selectivity against other members of the conventional, novel, and atypical isoforms of PKC as shown by lower potency in Table 1. Inhibition of PKC delta has been shown to lead to B-cell lymphoproliferative conditions and autoimmune disease in both animal studies and humans. Unlike other PKC inhibitors, Compound A does not inhibit PKC delta to any appreciable degree. Conversely, PKC beta inhibition has been shown to block B-cell function and proliferation. Therefore, the isoform selective properties of Compound A suggest a safety and efficacy advantage over non-specific PKC inhibitors.

TABLE 1

Inhibition of PKC isoforms by Compound A

| In Vitro Assays | $IC_{50}$ (nM) | Ki (nM) |
|---|---|---|
| Human PKC alpha |  | 10.4 |
| Human PKC betaII |  | 5.3 |
| Human PKC alpha | 2.3 |  |
| Human PKC betaI | 8.1 |  |
| Human PKC betaII | 7.6 |  |
| Human PKC delta | >1000 |  |
| Human PKC epsilon | 808 |  |
| Human PKC gamma | 57.5 |  |
| Human PKC eta | >1000 |  |
| Human PKC iota | >1000 |  |
| Human PKC theta | 25.6 |  |
| Human PKC zeta | >1000 |  |
| Human PKC mu | 314 |  |
| Human PRKCN (PKD3) | 131 |  |

Example 2: Compound A Exhibits Dose Dependent Inhibition of DLBCL Cell Proliferation Constitutive activation of the NF-κB pathway is a molecular hallmark of the activated B-celllike (ABC) subtype of diffuse large B-cell lymphoma (ABC-DLBCL) cells and is required for their proliferation and survival. NF-κB pathway activation leads to the induction of IL-6, which promotes the proliferation and survival of B cells.

To demonstrate that Compound A was capable of inhibiting the proliferation and survival of DLBCL cells with constitutive activation of NF-κB, the DLBCL cell lines TMD8, HBL1, and OCI-Ly3 were tested containing in an IL-6-based cell proliferation assay. Both TMD8 and HBL1 cells contain activating CD79 mutations, while OCI-Ly3 cells do not.

Cell Culture Conditions

TMD8 cells were grown in MEM media supplemented with 10% fetal calf serum (FCS), non-essential vitamin mix, and penicillin-streptomycin antibiotics (pen-strep). HBL1 cells were grown in RPMI-1640 media supplemented with 10% FCS and pen-strep. OCI-Ly3 cells were grown in DATEM media with 15% FCS, non-essential vitamin mix, pen-strep, and 25 mM HEPES buffer. Cells were maintained in suspension culture, fed twice weekly, and split 1:3 approximately every two weeks (TMD8, OCI-Ly3) or weekly (HBL1).

IL-6 Assay

Cells were harvested via centrifugation and resuspended twice to rinse the media of any IL-6. Cells were then plated in 96 well plates at $5 \times 10^5$ cells per well and exposed to increasing concentrations of Compound A, sotrastaurin, or media containing 0.1% DMSO (negative control). For each cell type, experiments were performed in the media used for growth and maintenance. Cells were allowed to grow for 48 hours after plating in the presence of inhibitors. Following compound exposure, cells were pelleted in the 96 well plate, supernatant was removed, and the concentration of IL-6 in the supernatant was determined using R&D Systems Haman IL-6 Quantikine® ELISA Kit (D6050) according to manufacturer's instructions.

Cell Proliferation and Survival Assay

Cells were cultured and maintained as described above, with cells always fed on the day prior to assay. Proliferation and survival of cells was quantified using an MTT assay kit according to manufacturer's instructions (Cell Proliferation Kit 1, Roche Diagnostics, Cat. No. 11 465 007 001). Experiments were performed in the same media used by each cell type for growth and maintenance. Cells ($5 \times 10^4$) were plated in 96 well plates and allowed to grow for 96 hours in the presence of inhibitors. After the exposure period was completed, MTT reagent was added for 3-4 hours. The MTT solubilization reagent was then added to stop the reaction and cells were incubated overnight at 37° C. The plate read the next day according to the kit instructions.

Results

Figure 1B:
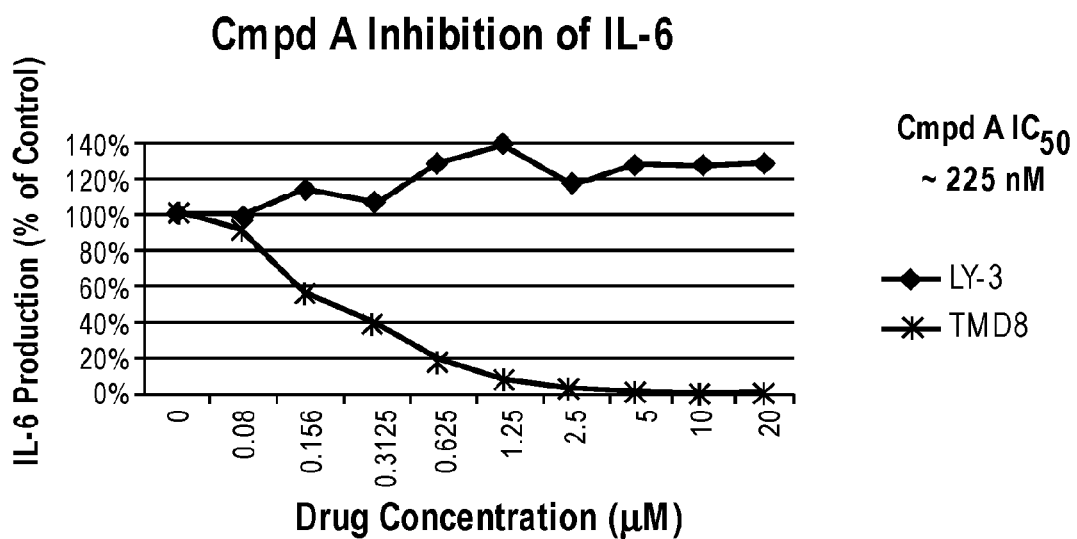

The results of a representative IL-6 assay are shown in FIGS. 1A-B and shows the dose dependent inhibition of IL-6 production in TMD8 and OCI-Ly3 cells exposed to Compound A (FIG. 1B) or sotrastaurin (FIG. 1A). The multi-isoform PKC inhibitor sotrastaurin has previously been shown to reduce IL-6 production and was utilized as a positive control. Compound A demonstrated a dose-dependent inhibition of IL-6 when tested in constitutively active CD79 mutant TMD8 and HBL1 (data not shown) cell lines suggesting successful inhibition of the NF-kB pathway signaling. Conversely, OCI-Ly3 cells lacking activating mutations in CD79 were not affected by either compound. The isoform specific PKC inhibitor Compound A was demonstrated to be slightly more potent compared to sotrastaurin.

Figure 2A:
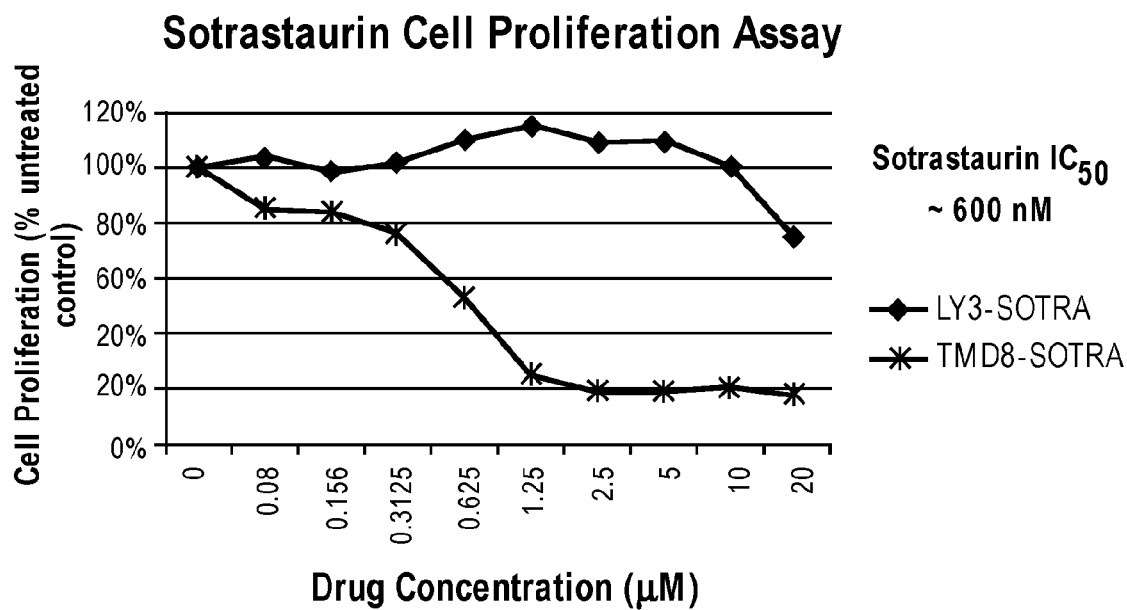
FIGS. 2A-B shows the dose dependent inhibition of cell proliferation and survival in TMD8 and OCI-Ly3 cells exposed to Compound A (FIG. 2B) or sotrastaurin (FIG. 2A).
Figure 2B:
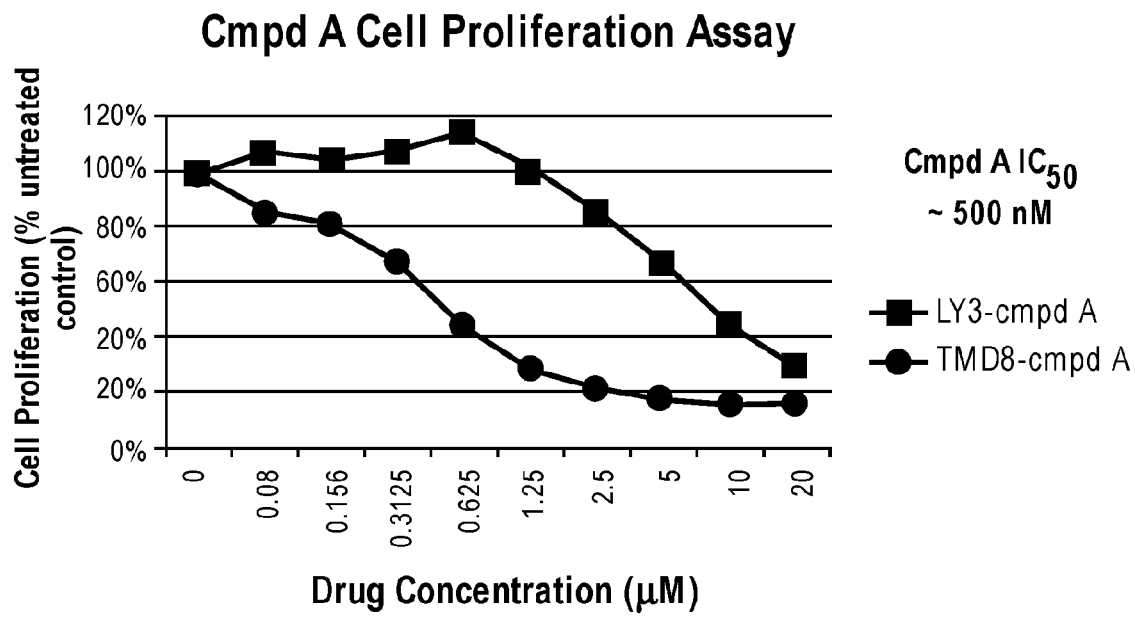

The results of a representative cell proliferation assay are shown in FIGS. 2A-B and displays the dose dependent inhibition of cell proliferation and survival in TMD8 and OCI-Ly3 cells exposed to Compound A (FIG. 2B) or sotrastaurin (FIG. 2A). The multi-isoform PKC inhibitor sotrastaurin has previously been shown to inhibit DLBCL cell proliferation and survival and was utilized as a positive control. Compound A demonstrated a dose-dependent inhibition of cell proliferation and survival when tested in constitutively active CD79 mutant TMD8 and HBL1 (data not shown) cell lines. Conversely, OCI-Ly3 cells lacking activating mutations in CD79 were not affected by either compound except at the highest doses tested. The isoform specific PKC inhibitor Compound A was demonstrated to be modestly more potent compared to sotrastaurin.

Figure 3A:
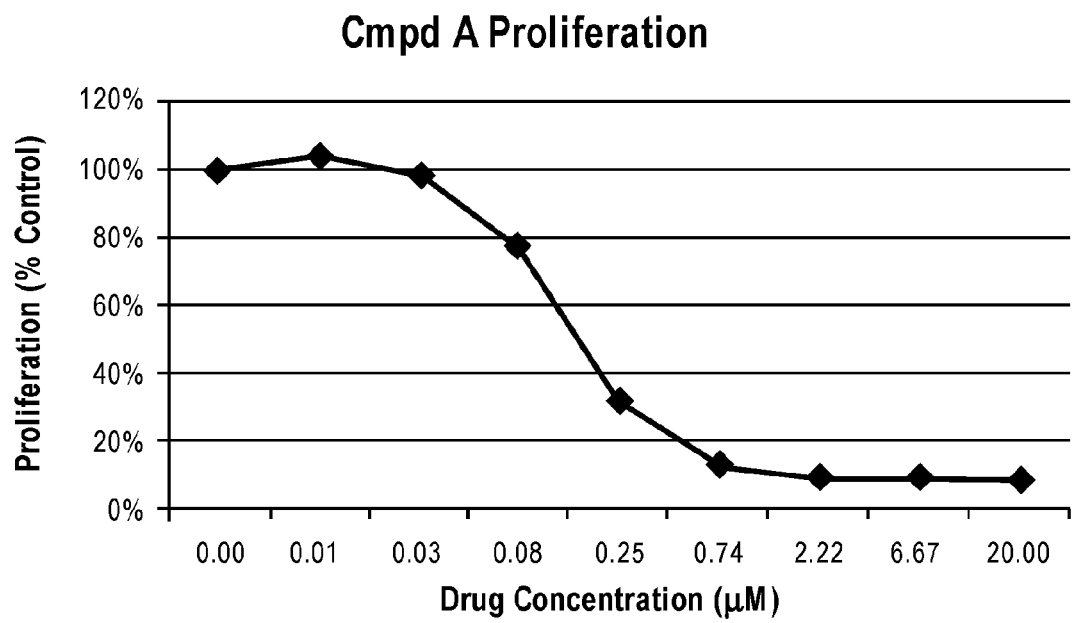
FIGS. 3A-C shows single agent treatment of TMD8 cells with either Compound A (FIG. 3A), ibrutinib (FIG. 3B), or combination treatment with Compound A and ibrutinib (FIG. 3C).
Figure 3B:
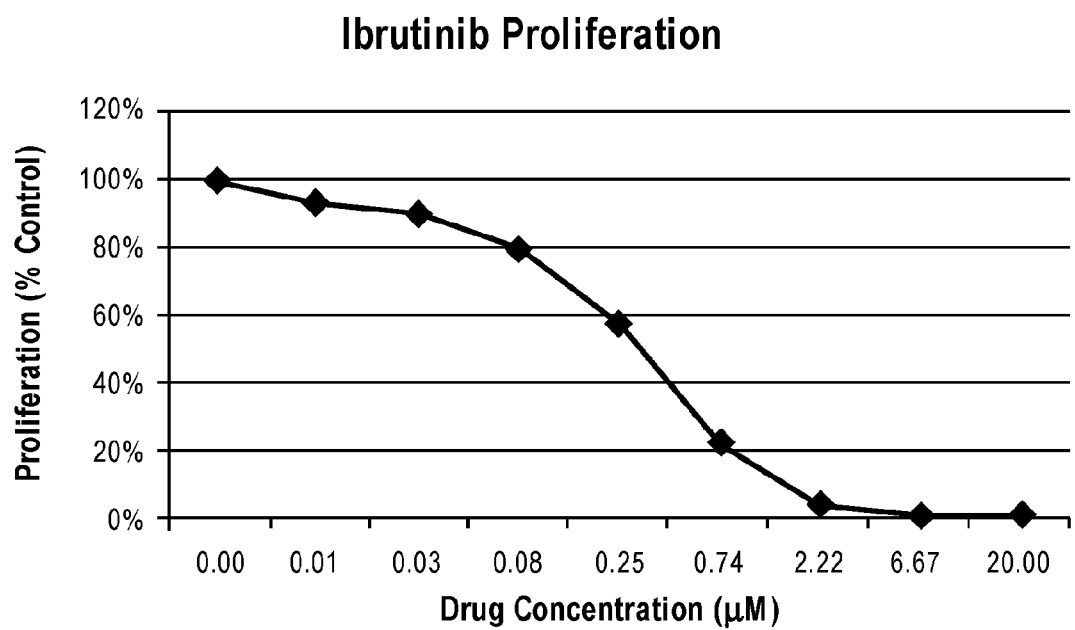
Figure 3C:
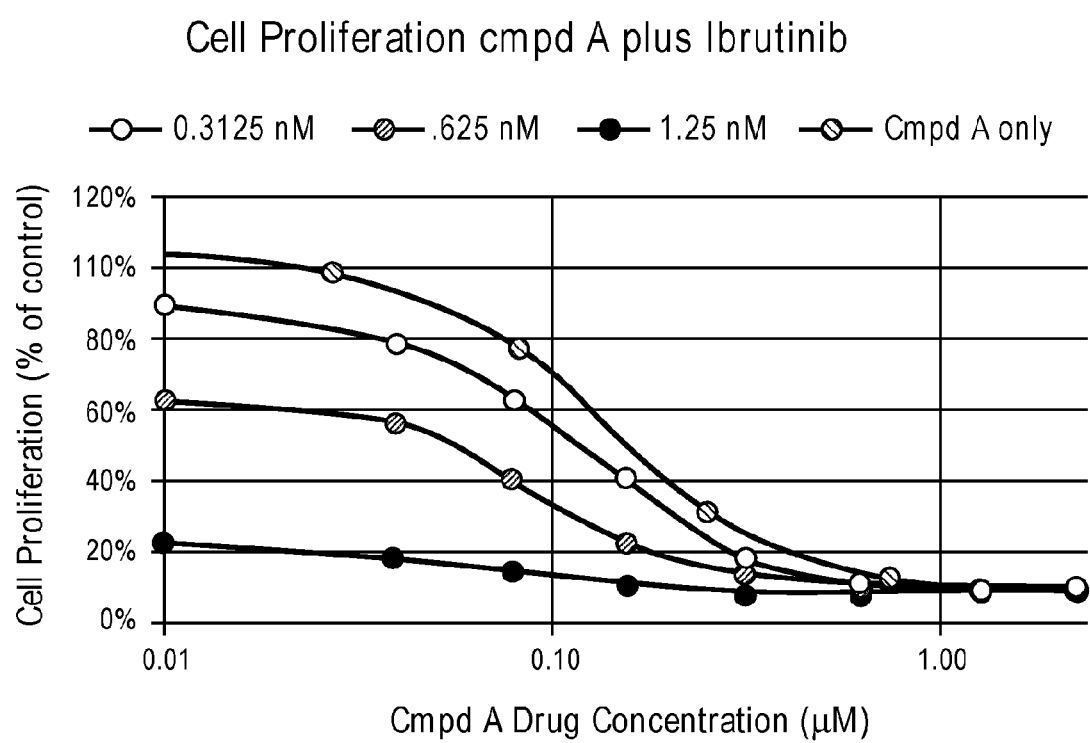

Example 3: Compound A and Ibrutinib Synergistically Reduce the Proliferation of DLBCL Cells The combinatorial effects of Compound A and ibrutinib were tested constitutively active TMD8 DLBCL cells. OCI-Ly3 cells were utilized as a negative control (results not shown). Single compound treatment of TMD8 cells are shown in FIG. 3A (Compound A) and FIG. 3B (ibrutinib). Treatment with various ratios of Compound A and ibrutinib are shown in FIG. 3C and demonstrate that the combination of Compound A and ibrutinib decreases TMD8 cell proliferation greater than either compound alone. To determine if the decreases cell proliferation was an additive or synergistic effect, the resulting dose response curves were examined by the Chou-Talalay method (Chou T C, Drug Combination Studies and Their Synergy Quantification Using the Chou-Talalay Method. Cancer Res, 2010, 70: 440-6) and the Webb Summation (fractional product) approach (Chou T C, Theoretical basis, experimental design, and computerized simulation of synergism and antagonism in drug combination studies. Pharmacol Rev., 2006, 58:621-81). Both methodologies similarly found modest synergy in the mid-portion of the dose response curve for Compound A (i.e., from about 80-750 nM).

Example 4: In Vivo Anti-Proliferative Activity of Compound A in a Mouse Xenograph Model of DLBCL To test the efficacy of Compound A in vivo, TMD8 cells were grown and subcutaneously injected into SCID mice. Large scale suspension culture of TMD8 cells was performed in T250 flasks, where cells were expanded weekly. Animals (n=24) were inoculated with $10\times10^6$ cells ($10\times10^6$ cells in 100 µL, volume of 50% Matrigel®) subcutaneously in the animal's right flank. Dosing of 120 mg/kg; BID Compound A was initiated on Day 14, the first day after which tumors had exceeded the pre-determined tumor volume.

Figure 4:
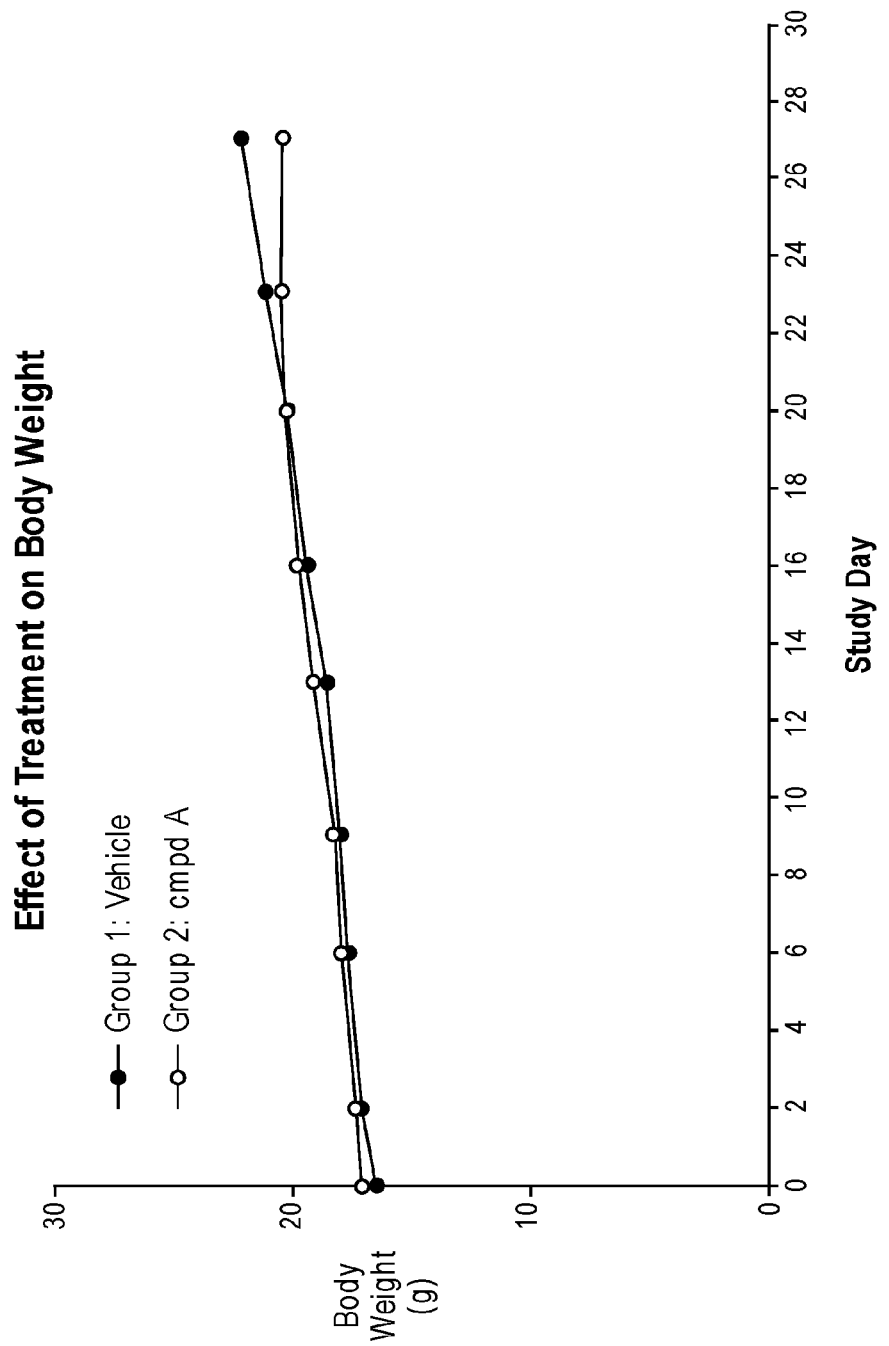
FIG. 4 shows the effect of Compound A treatment on body weight in a TMD8 cell mouse xenograph model of DLBCL.
Figure 5:
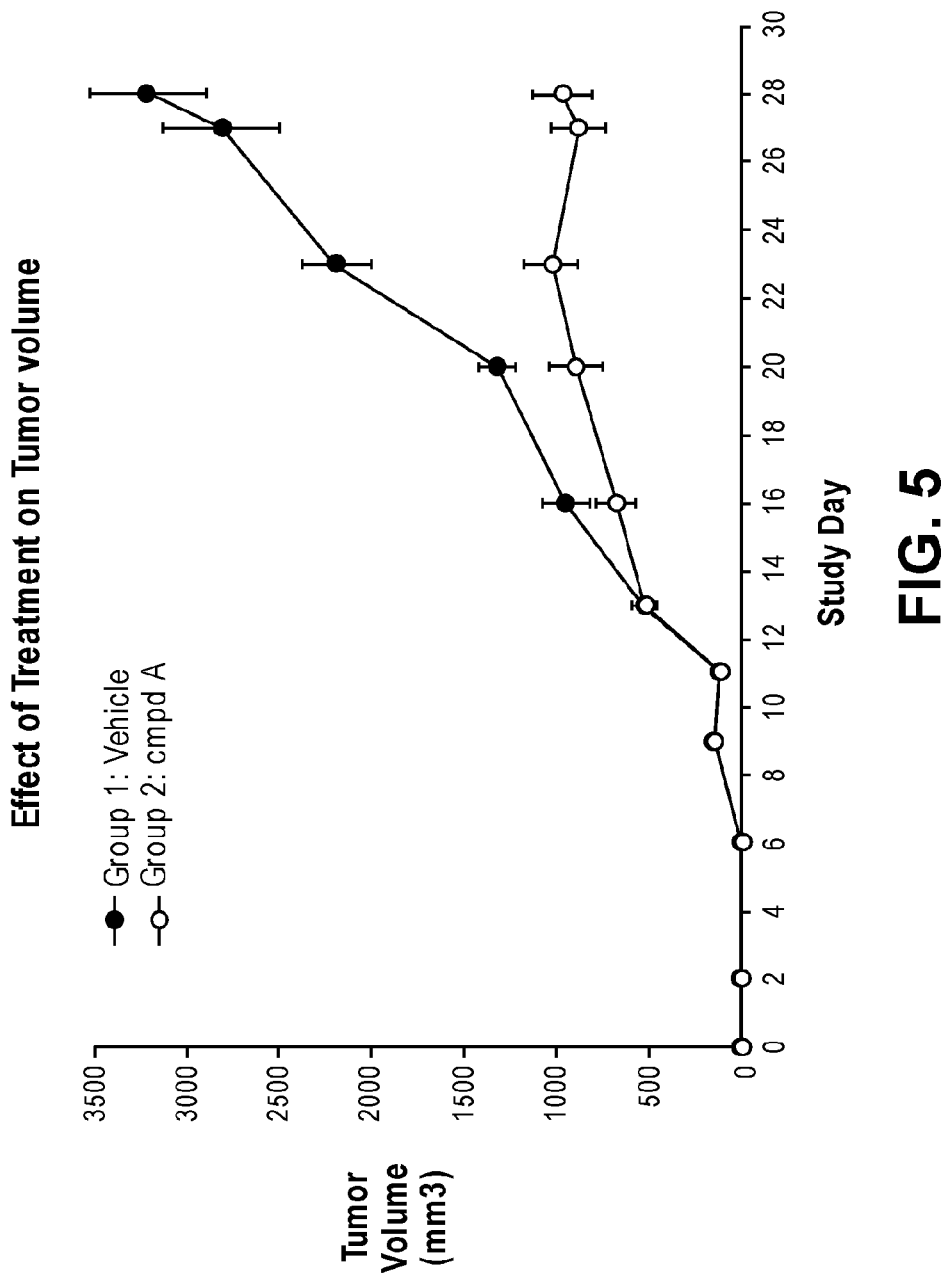
FIG. 5 shows the effect of Compound A treatment on tumor volume in a TMD8 cell mouse xenograph model of DLBCL.

As shown in FIG. 4, a steady, slow increase in body weight was evident in both control and Compound A treated animals for the first 10 days of treatment. In the Compound A treated group, there was no increase in body weight from day 24-28. Conversely, vehicle treated animals continued to gain weight from day 24-28 at approximately the same rate. As seen in FIG. 4, the mean weight in the vehicle treated group was 1.8 g greater than the weight of Compound A treated animals. As seen in FIG. 5, the difference in weight may have been due mainly to the larger tumor mass observed in vehicle treated animals.

As shown in FIG. 5, the effect of Compound A treatment on tumor growth was striking. After just two days of dosing, a trend toward significant differences in tumor volume was noted. In Compound A treated mice, there was no appreciable amounts of tumor growth observed from study days 20 to 28, the last day of measurement. During this time period, mean tumor volume increased from 898 mm$^3$ to 970 mm$^3$, an increase of just 8%. In contrast, during this same time period, the mean tumor volume in the control group increased from 1324 mm$^3$ to 3207 mm$^3$, an increase of more than 2.4 fold, i.e., an increase in volume of 142%.

Example 5: In Vivo Effect on Peripheral Lymphocyte Levels

Figure 6:
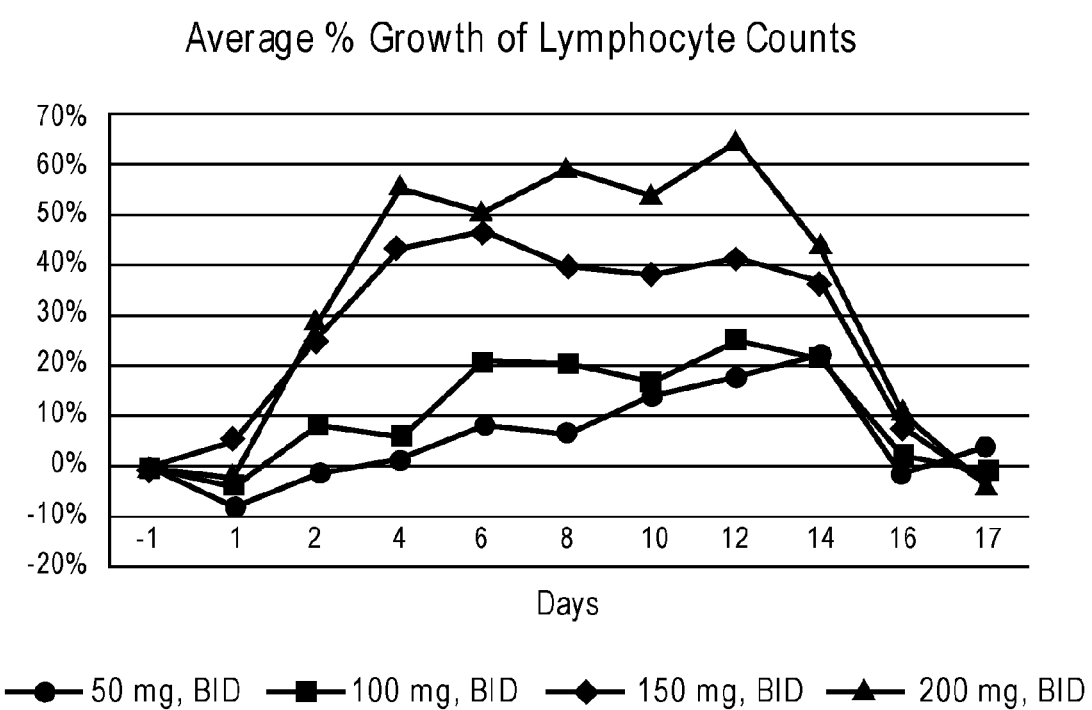
FIG. 6 shows the lymphocyte count in a human subject treated with Compound A in a multiple ascending dose study.

Normal, healthy human patients received various doses of Compound A for 14 days of dosing. The dose levels were as follows: cohort 1: 50 mg, BID; cohort 2: 100 mg, BID; cohort 3, 150 mg, BID; and cohort 4, 200 mg BID. Blood samples harvested from treated patients and a dose dependent increase in the number of circulating lymphocytes was observed (FIG. 6). Ibrutinib, a Bruton's tyrosine kinase (BTK) inhibitor, also leads to an increase in B cells in the peripheral circulation. This lymphocytosis effect strongly supports the hypothesis that Compound A is active in the BCR- NF-kB pathway.

Example 6: In Vivo Anti-Proliferative Activity of Compound A in a Mouse Model of CLL An in vivo model of ibrutinib resistant CLL has been developed (Lapalombella, et al. Blood (2012), 120:4621-34; Woyach, et al. Blood (2014), 123:1207-13; Hing, et al. Blood (2015), 125:3128-3132). Mice (C57BL/6) are engrafted with splenocytes derived from ibrutinib-resistant Eµ-TCL1 mice that are previously passaged through 2 C57BL/6 animals. Ibrutinib-resistant Eµ-TCL1 mice are generated by continuous dosing of animals with ibrutinib in drinking water from the time of weaning. Ibrutinib-resistant Eµ-TCL1 mice with active leukemia are divided into test and control cohorts and the test cohort is administered an oral gavage dose of compound A, 120 mg/kg, BID for 14 days. On day 15, both test and control cohorts are injected intraperitoneally with 100 µg EdU (5-ethynyl-29-deoxyuridine), and 2-4 hours post injection single-cell suspensions are prepared from spleen and bone marrow tissue samples. From these samples EdU incorporation is detected by flow cytometry to determine cell proliferation.

What is claimed is:

1. A method of treating a hematological malignancy in an individual in need thereof, comprising administering to the individual a pharmaceutical composition comprising 5-{[(2S,5R)-2,5-dimethyl-4-(tetrahydro-2H-pyran-4-ylmethyl)piperazin-1-yl]carbonyl}—N—(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, wherein the hematological malignancy is relapsed or refractory chronic lymphocytic leukemia (CLL).

2. The method of claim 1, wherein use of ibrutinib in the treatment of said hematological malignancy is unsuitable or otherwise contraindicated.

3. The method of claim 1, wherein the relapsed or refractory chronic lymphocytic leukemia (CLL) is refractory to a BTK inhibitor.

4. The method of claim 3, wherein the BTK inhibitor is ibrutinib.

5. The method of claim 1, wherein the relapsed or refractory chronic lymphocytic leukemia (CLL) is relapsed after treatment with a BTK inhibitor.

6. The method of claim 5, wherein the BTK inhibitor is ibrutinib.

7. The method of any one of claim 1, 2, 3, 4, 5, or 6 wherein the method is characterized by the occurrence of lymphocytosis.

* * * * *